(12) United States Patent
Montry

(10) Patent No.: US 11,298,391 B1
(45) Date of Patent: Apr. 12, 2022

(54) TOPICAL SKIN HEALTH IMPROVEMENT COMPOSITIONS AND ADMINISTRATIONS THEREOF

(71) Applicant: Lorenol Laboratories, Inc., Austin, TX (US)

(72) Inventor: Laura Montry, The Colony, TX (US)

(73) Assignee: Lorenol Laboratories, Inc., Austin, TX (US)

( * ) Notice: Subject to any disclaimer, the term of this patent is extended or adjusted under 35 U.S.C. 154(b) by 0 days.

(21) Appl. No.: 15/965,473

(22) Filed: Apr. 27, 2018

Related U.S. Application Data

(60) Provisional application No. 62/490,999, filed on Apr. 27, 2017.

(51) Int. Cl.

| | |
|---|---|
| *A61K 36/31* | (2006.01) |
| *A61K 36/906* | (2006.01) |
| *A61K 36/00* | (2006.01) |
| *A61K 47/44* | (2017.01) |
| *A61K 47/22* | (2006.01) |
| *A61K 47/20* | (2006.01) |
| *A61K 9/00* | (2006.01) |
| *A61P 17/02* | (2006.01) |
| *A61K 9/06* | (2006.01) |
| *A61K 36/28* | (2006.01) |
| *A61K 31/045* | (2006.01) |
| *A61K 36/9068* | (2006.01) |

(52) U.S. Cl.
CPC ............ *A61K 36/31* (2013.01); *A61K 9/0014* (2013.01); *A61K 9/06* (2013.01); *A61K 47/20* (2013.01); *A61K 47/22* (2013.01); *A61K 47/44* (2013.01); *A61P 17/02* (2018.01); *A61K 31/045* (2013.01); *A61K 36/28* (2013.01); *A61K 36/9068* (2013.01); *A61K 2300/00* (2013.01)

(58) Field of Classification Search
None
See application file for complete search history.

(56) References Cited

U.S. PATENT DOCUMENTS

| | | | | |
|---|---|---|---|---|
| 7,524,816 | B2 * | 4/2009 | Day | C07K 7/06 514/1.1 |
| 8,246,969 | B2 | 8/2012 | Engles et al. | |
| 8,246,971 | B2 | 8/2012 | Engles et al. | |
| 8,268,336 | B2 | 9/2012 | Engles et al. | |
| 8,496,951 | B2 | 7/2013 | Engles et al. | |
| 9,107,874 | B2 | 8/2015 | Engles et al. | |
| 2004/0254252 | A1 | 12/2004 | Engles et al. | |
| 2014/0271525 | A1 * | 9/2014 | Florence | A61K 36/28 424/78.03 |
| 2015/0342854 | A1 * | 12/2015 | Shibuya | A61Q 19/08 424/62 |
| 2016/0228352 | A1 * | 8/2016 | Lewis | A61K 35/618 |
| 2018/0085486 | A1 * | 3/2018 | Chen | A61L 15/18 |

FOREIGN PATENT DOCUMENTS

| | | | |
|---|---|---|---|
| EP | 3153214 A1 * | 4/2017 | |
| FR | 2824475 A1 * | 11/2002 | |
| KR | 2012077219 A * | 7/2012 | |
| WO | WO2007042472 A1 * | 4/2007 | |

\* cited by examiner

*Primary Examiner* — Michael Barker
*Assistant Examiner* — Randall O Winston
(74) *Attorney, Agent, or Firm* — Ferguson Braswell Fraser Kubasta PC; Elizabeth Philip Dahm; Kelly J. Kubasta

(57) ABSTRACT

In various implementations, a skin therapeutic may be topically applied to improve skin health. The skin therapeutic may decrease inflammation, decrease redness, and/or decrease health times. The skin therapeutic may include a composition that includes two or more of *Brassica olearacea italica* Seed Oil, bisabolol, and/or *Zingiber officinales*.

20 Claims, 2 Drawing Sheets

TOPICAL SKIN HEALTH IMPROVEMENT COMPOSITIONS AND ADMINISTRATIONS THEREOF

CROSS-REFERENCE TO RELATED APPLICATION

This application claims the benefit of priority to U.S. Provisional Patent Application No. 62/490,999 entitled "Topical Skin Health Improvement Compositions" filed on Apr. 27, 2017, and which is incorporated by reference herein for all purposes.

TECHNICAL FIELD

The present invention relates to compositions that improve skin health.

BACKGROUND

Skin condition after skin therapies and skin procedures is often poor. Healing is often slow and during healing, skin appearance may be red (e.g., which may prolong periods before returning to work and/or decrease user satisfaction with the skin therapy and/or procedure). In addition, many common skin products may make skin health worse. Thus, there is a need for a mixture to be applied on skin to improve skin health.

SUMMARY

In various implementations, a skin treatment may include a composition. The skin therapeutic composition may include two or more of *Brassica olearacea italica* Seed Oil, bisabolol, *Zingiber Officinales*, clove oil, and/or derivatives thereof. One or more of the compounds may be included in one or more different percentages to create skin treatments that include one or more skin therapeutic compositions. Usage of different percentages of the components may provide different effects on the skin with topical administration. The skin therapeutic composition(s) may be administered in various forms such as balms, serums, cleansers, lotions, etc. The skin therapeutic composition may be administered by topically applying the skin therapeutic composition on a user's skin or portions thereof. The skin therapeutic composition may be applied to healthy skin, skin undergoing treatment, and/or damaged skin (e.g., by skin treatment and/or other causes).

In various implementations, the skin therapeutic composition may be applied periodically (e.g., daily, twice daily, etc.) and/or based on user preference (e.g., to soothe skin). The skin therapeutic composition may be applied post skin treatments (e.g., ablative and/or non-ablative treatments including for example surgery, peels, and/or injections) to reduce the amount of time required to heal skin (e.g., when compared with not applying the skin therapeutic composition and/or when compared with applying moisturizers).

In various implementations, a topical skin composition may include approximately 0.025 to approximately 1 weight percent of *Zingiber Officinale*; at least approximately 0.15 weight percent of Bisabolol; and/or approximately 0.05 to approximately 10 weight percent of *Brassica olearacea italica* Seed oil. The topical skin composition may include at least two of *Zingiber Officinale*, Bisabolol, and *Brassica olearacea italica* Seed, in some implementations. The topical administration of the skin composition may improve skin health, for example, by reducing redness, inflammation, healing time, recovery time, visible effects of aging, etc.

Implementations may include one or more of the following features. The topical skin composition may include *Zingiber Officinale*, Bisabolol, and *Brassica Olearacea italica* Seed, in some implementations. The weight percent of Bisabolol may be greater than the weight percent of *Brassica olearacea italica* Seed oil in the skin composition. The topical skin composition may include a weight percentage of *Zingiber Officinale* of approximately 0.025 to approximately 0.1 weight percent of the skin composition, a weight percentage of Bisabolol of approximately 0.025 to approximately 0.1 weight percent of the skin composition, and a weight percentage of *Brassica olearacea italica* Seed oil of approximately 0.05 to approximately 0.1 weight percent of the skin composition. The topical skin composition may include approximately 5-10 weight percent of Sodium C-14-16 olefin sulfonate. Topical administration of the skin composition may cleanse the skin. In some implementations, the topical skin composition may include a weight percentage of *Zingiber Officinale* of approximately 0.025 to approximately 0.1 weight percent of the skin composition, a weight percentage of Bisabolol of at least approximately 0.025, and a weight percentage of *Brassica olearacea italica* Seed oil of approximately 6 to approximately 8 weight percent of the skin composition. The skin composition may include approximately 10-20 weight percent of sunflower oil. In some implementations, the topical skin composition may include a weight percentage of *Zingiber Officinale* of approximately 0.1 to approximately 0.3 weight percent of the skin composition, and a weight percentage of *Brassica olearacea italica* Seed oil of approximately 6 to approximately 8 weight percent of the skin composition. The skin composition may include approximately 4-6 weight percent of jojoba, lanolin, or mixtures thereof. The skin composition may be topically administered as a lip balm. In some implementations, the topical skin composition may include a weight percentage of *Zingiber Officinale* of approximately 0.5 to approximately 1.5 weight percent of the skin composition, and a weight percentage of Bisabolol of approximately 0.5 to approximately 1.5 weight percent of the skin composition. The skin composition may include approximately 0.1 to approximately 0.4 of silver (e.g., microsilver). The skin composition may include approximately 10 to approximately 20 weight percent of sunflower oil, in some implementations. Topical administration of the skin composition may soothe the skin (e.g., increase user satisfaction, reduce unpleasant tightness in skin, reduce redness, reduce dryness, and/or reduce inflammation). In some implementations, the topical skin composition may include a weight percentage of *Zingiber Officinale* of approximately 0.8 to approximately 1 weight percent of the skin composition, and a weight percentage of *Brassica olearacea italica* Seed oil of approximately 5 to approximately 10 weight percent of the skin composition. The skin composition may include approximately 0.5 to approximately 1.5 weight percent of sulforaphane. The skin composition may include approximately 4 to approximately 6 weight percent of sunflower oil. The skin composition may include approximately 1 to approximately 3 weight percent of retinyl palmitate. The skin composition may include *Brassica campestirs* (Rapeseed) Sterols. The skin composition may include approximately 4 to approximately 6 weight percent of sunflower wax and/or another wax. In some implementations, the topical skin composition may include a weight percentage of *Zingiber Officinale* of approximately 0.1 to approximately 0.2 weight percent of the skin composition, a weight percentage of Bisabolol of approximately 0.15 to approximately 0.2 weight percent of the skin composition, and a weight percentage of *Brassica olearacea italica* Seed oil of approximately 5 to approximately 10 weight percent of the skin composition. The skin composition may include approximately 6 to approximately 8 of Tetrahexyl Ascorbate, Vitamin C, or mixtures thereof. In some implementations, the topical skin composition may improve skin health by reducing redness, reducing inflammation, reducing skin recovery time, and/or reducing dryness. The topical skin composition may be applied to healthy skin.

In various implementations, the skin composition may be topically administered to improve skin health. For example, a therapeutically effective amount of a skin composition may be topically administered (e.g., on at least a portion of the skin and/or proximate a portion of the skin) to reduce inflammation and/or redness of skin. The skin composition may include approximately 0.025 to approximately 1 weight percent of *Zingiber Officinale*; at least approximately 0.15 weight percent of Bisabolol; and/or approximately 0.05 to approximately 10 weight percent of *Brassica olearacea italica* Seed oil. The topical skin composition may include at least two of *Zingiber Officinale*, Bisabolol, and *Brassica olearacea italica* Seed.

Implementations may include one or more of the following features. The topical skin composition may include *Zingiber Officinale*, Bisabolol, and *Brassica* Olearacea *italica* Seed, in some implementations. The skin composition may be topically administered to burned skin and/or dry skin. The skin composition may be topically administered after one or more skin treatments, such as but not limited to, surgery, chemical peel, mircroneedling, microderm abrasion, injections, ablative laser therapy, and/or non-ablative laser therapy. The skin composition may be topically administered prior to one or more skin treatments, in some implementations.

In various implementations, a therapeutically effective amount of the skin composition may be topically administering on at least a portion of the skin to increase the rate of skin healing. The skin composition may include approximately 0.025 to approximately 1 weight percent of *Zingiber Officinale*; at least approximately 0.15 weight percent of Bisabolol; and/or approximately 0.05 to approximately 10 weight percent of *Brassica olearacea italica* Seed oil. The topical skin composition may include at least two of *Zingiber Officinale*, Bisabolol, and *Brassica olearacea italica* Seed.

Implementations may include one or more of the following features. The topical skin composition may include *Zingiber Officinale*, Bisabolol, and *Brassica* Olearacea *italica* Seed, in some implementations. Topically administering the skin composition may decrease dryness (e.g., which may increase the rate of skin healing). Topically administering the skin composition may decrease scarring, in some implementations. The skin composition may be topically administered after one or more skin treatments, such as but not limited to, surgery, chemical peel, and/or tattoo removal treatment. The topical administration of the skin composition may provide (e.g., and thus increase a rate of skin healing) a protective barrier to water loss by the skin and/or reduction of reaction by the skin to irritants. In some implementations, the weight percentage of *Zingiber Officinale* is approximately 0.025 to approximately 0.1 weight percent of the skin composition, and the weight percentage of Bisabolol is at least approximately 0.025, and the weight percentage of *Brassica olearacea italica* Seed oil is approximately 6 to approximately 8 weight percent of the skin composition. The skin composition may include approximately 10-20 weight percent of sunflower oil.

In some implementations, kits may be created that include one or more of the skin therapeutic compositions. The kits may be for predetermined administration regimens (e.g., daily treatment, anti-aging, post-treatment, burn, dry skin, healing, repairing, soothing, etc.).

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which.

Like reference symbols in the various drawings indicate like elements.

DETAILED DESCRIPTION

Figure 1:
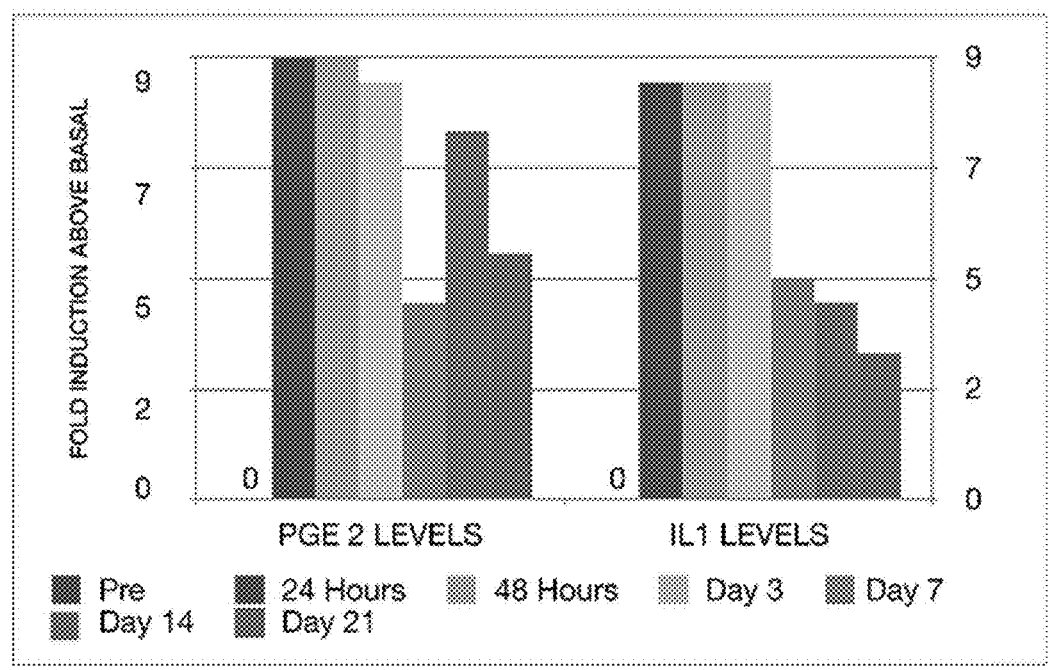
FIG. 1 illustrates an implementation of an example chart illustrating long term post-laser treatment skin inflammation.

In various implementations, a skin therapeutic may include a composition that improves skin health. The composition may be topically applied to a user's skin. For example, the skin therapeutic may be applied to a skin surface and/or may be at least partially absorbed into the skin. The skin therapeutic composition(s) may be administered in various forms such as balms, serums, cleansers, lotions, and/or any other appropriate form. In some implementations, topical administration of the skin therapeutic may reduce inflammation, reduce redness, and/or decrease recovery time (e.g., post-operation and/or skin treatment, such as skin resurfacing). The topical application may provide an anti-aging treatment (e.g., to provide a visible improvement in aging symptoms such as skin tightness, redness, and/or wrinkles) to healthy skin, in some implementations. User satisfaction of topical application may be increased (e.g., when compared with other skin treatment products) by properties of the preparations that include the skin composition, such as feel on skin and/or ease of use (e.g., approximately homogenous mixture). The skin therapeutic composition may be applied pre-skin treatment, post-skin treatment, post-skin damage, and/or as desired by a user (e.g., to soothe and/or repair dry skin, to promote healing in cuts, and/or to promote healing in burns).

User satisfaction with a treatment (e.g., medical treatments such as in-office treatments and/or surgical treatments; and/or cosmetic treatments) may be increased with application of skin therapeutic composition(s) since immediate and/or later skin appearance may be improved (e.g., by reducing redness and/or inflammation and/or decreasing recovery time). User satisfaction with a skin treatment may be increased because topical application of one or more skin therapeutics post-treatment may reduce undesirable side effects of treatments, such as inflammation, redness, dryness, etc.

The skin therapeutic compositions may include two or more of *Brassica olearacea italica* Seed Oil, bisabolol,

*Zingiber Officinales*, clove oil, and/or derivatives thereof. In various implementations, skin therapeutic compositions may include: *Brassica olearacea italica* Seed Oil and/or derivatives thereof; and, one or more of bisabolol, *Zingiber Officinales*, clove oil, and/or derivatives thereof. The combination of the two or more of *Brassica olearacea italica* Seed Oil, bisabolol, *Zingiber Officinales*, and/or clove oil may provide benefits that are greater than their additive properties (e.g., properties when compounds are used singularly). For example, inflammation, recovery time, redness, and/or scarring may be decreased more by using the composition than when using the components of the composition separately.

*Brassica olearacea italica* Seed Oil may be utilized rather than other forms of compounds produced from broccoli, in some implementations. The *Brassica* Olearacea *italica* Seed Oil may be more effective at improving skin health than other forms of compounds from broccoli. For example, the *Brassica olearacea italica* Seed Oil may include 100 times more, by weight, of glucoraphanin than broccoli stalks and florets. The composition may include approximately 0.1 to approximately 20 percent by weight of *Brassica olearacea italica* Seed Oil.

The composition may include approximately 0.05 to approximately 20 percent by weight of bisabolol. The composition may include less than approximate 10 percent by weight of bisabolol. The composition may include more *Brassica olearacea italica* Seed Oil than bisabolol, in some implementations.

The composition may include approximately 0.5 to approximately 20 percent by weight of *Zingiber Officinales*. The composition may include less than approximate 10 percent by weight of *Zingiber Officinales*. The composition may include more bisabolol than *Zingiber Officinales*. In some implementations, the composition may include approximately the same amount (e.g., by weight) of bisabolol and *Zingiber Officinales*.

In some implementations, the *Brassica olearacea italica* Seed Oil, bisabolol, *Zingiber Officinales*, and/or clove oil may be provided in purified and/or unpurified forms. In some implementations, the *Brassica olearacea italica* Seed Oil, bisabolol, and/or *Zingiber Officinales* may be provided in combination with one or more other compounds.

In some implementations, the skin therapeutic composition may include *Brassica olearacea italica* Seed Oil, bisabolol, and *Zingiber Officinales*. The skin therapeutic composition may include approximately 0.1 percent to approximately 20 percent of *Brassica olearacea italica* Seed Oil, 0.05 percent to approximately 20 percent of bisabolol, and approximately 0.05 to approximately 20 percent of *Zingiber Officinales*. In some implementations, the skin therapeutic composition may include approximately 0.1 percent to approximately 10 percent of *Brassica olearacea italica* Seed Oil, 0.05 percent to approximately 5 percent of bisabolol, and approximately 0.05 to approximately 5 percent of *Zingiber Officinales*.

In some implementations, the skin therapeutic composition may include *Brassica olearacea italica* Seed Oil and clove oil. The skin therapeutic composition may include approximately 0.1 percent to approximately 20 percent of *Brassica olearacea italica* Seed Oil and approximately 0.05 percent to approximately 20 percent of clove oil. The skin therapeutic composition may include approximately 0.1 percent to approximately 10 percent of *Brassica olearacea italica* Seed Oil and approximately 0.1 percent to approximately 10 percent of clove oil.

In various implementations, one or more additional compositions may be included in a skin therapeutic composition. For example, the skin therapeutic composition may include a sulfonate, sulforaphane, a glyceryl behenate compound (e.g., glyceryl behenate and/or glyceryl debehenate), tribehenin, waxes (e.g., sunflower wax and/or a wax mixture of glyceryl debehenate, tribehenin, and/or glyceryl behenate), sunflower oil (e.g., *Helianthus annuus* seed oil), ethyl vanillin, sunflower seed oil, heyxldecanol, cetylhydroxyproline palmitamide, witch hazel, *Commiphora myrrha* resin extract, menthol, fragrance(s) (e.g., spearmint oil and/or peppermint oil), glycerin, oat (e.g., *Avena sativa* extract), chamomile, glycols (e.g., butylene glycol and/or pentylene glycol), hydroxyphenyl propamidobenzoid, aloe, Trideceth-9, PEG-5 Isononanoate, water, silver, retinoid (e.g., retinyl palmitate and/or retinoic acid), vitamin C, tetrahexyl ascorbate, any other appropriate additional composition, and/or mixtures thereof. The additional compositions may increase benefits provided by the skin therapeutic (e.g., reduce redness, inflammation, and/or recovery time) and/or may improve the formulation (e.g., consistency, color, smell, etc.).

For example, the skin therapeutic composition may include one or more additional ingredients such as sunflower seed oils and/or waxes that include sunflower seed oil. For example, the skin therapeutic may include approximately 1 to approximately 20 percent, by weight, of sunflower seed oil. The amount of sunflower seed oil and/or wax may be based on the consistency selected for a product including the skin therapeutic. For example, a balm may include more sunflower seed wax than a serum.

In some implementations, inclusion of a wax in the skin therapeutic composition may facilitate homogenization of the skin therapeutic composition. The wax may include natural waxes (e.g., sunflower wax) and/or synthetic waxes (e.g., a mixture of glyceryl debehenate, tribehenin, and/or glyceryl behenate). For example, since the skin therapeutic compositions may include a high number of oils and/or may include combinations of oils and water based compounds, mixing the compounds may be difficult and/or mixing the compounds with water-based ingredients may be difficult. As another example, *Brassica olearacea italica* Seed Extract may have difficulty mixing with oils. The inclusion of a wax based product, such as a wax that includes sunflower seed oil, sunflower oil, beeswax, and/or another wax mixture (e.g., glyceryl debehenate, tribehenin, and/or glyceryl behenate) may facilitate mixing of the ingredients such that the product does not separate. Users to become dissatisfied with a product in which mixing is required prior to application; and thus, a wax and/or oil to incorporate ingredients may be utilized.

In some implementations, the skin therapeutic compositions may include sulforaphane and two or more of *Brassica olearacea italica* Seed Oil, bisabolol, *Zingiber Officinales* and/or derivatives thereof.

In some implementations, the skin therapeutic compositions may include surfactants to create a cleanser that includes the skin therapeutic compositions. Sulforaphane may be an antioxidant that improves recovery results (e.g., skin healing) and/or times. Inclusion of the sulforaphane in the composition may improve skin appearance and/or decrease healing time more quickly than when sulforaphane is used independently.

In some implementations, the skin therapeutic compositions may include fragrances. The included fragrances may be non-irritating since skin therapeutic compositions may be utilized post-skin procedures. The fragrance may be selected based on the type of product. For example, a lip balm may include a mint (e.g., spearmint and/or peppermint oil). A night serum may include a calming fragrance (e.g., chamomile and/or lavender). A daily serum and/or cleanser may include a mood lifting scent (e.g., based on common aromatherapy knowledge).

The skin therapeutic compositions may be provided in any appropriate delivery form. For example, the skin therapeutic composition may be provided as a gel, serum, cream, liquid, mist, etc. Any appropriate binder(s) may be utilized to produce the selected delivery form. For example, sunflower oil as a wax may be utilized to generate a cream that combines oils and/or water based ingredients. As another example, a mixture of glyceryl debehenate, tribehenin, and/or glyceryl behenate may be utilized to gel ingredients together. In some implementations, approximately 10% to approximately 15% (e.g., by weight) of a mixture of glyceryl debehenate, tribehenin, and/or glyceryl behenate may be utilized to produce a serum and inhibit liquefaction of a skin therapeutic composition. In some implementations, a mixture of glyceryl debehenate, tribehenin, and/or glyceryl behenate may be utilized in a percentage greater than approximately 15, by weight, to produce a balm and inhibit liquefaction. In some implementations, the amount of an ingredient may be limited to produce a specified delivery form. For example, to produce a serum or balm, the amount of *Brassica olearacea italica* Seed Oil may be approximately 7 percent or less, by weight. In some implementations, inhibiting liquefaction of the skin composition may improve results (e.g., since the ratios of the ingredients in the composition may be approximately maintained) and/or may increase user satisfaction with the application (e.g., since the composition may have a smooth feel, since the user may not need to shake or otherwise mix the composition prior to application, etc.).

In some implementations, the skin therapeutic may be a first skin therapeutic. The first skin therapeutic may include *Zingiber Officinales*, bisabolol (e.g., from German chamomile, *Matricaria recutita*, and/or *Myoporum crassifolium*), and *Brassica* Olearacea *italica* Seed Extract. The *Zingiber Officinales* may be approximately 0.1 to approximately 10 percent by weight of the first skin therapeutic. For example, the first skin therapeutic may include approximately 0.05 percent to approximately 5 percent by weight of *Zingiber Officinales*. In some implementations, the first skin therapeutic extract may include less than 1 percent by weight of *Zingiber Officinales*. The amount of *Zingiber Officinales* may be a quantity that does not cause irritation of the skin (e.g., less than 1 percent by weight). The bisabolol may be approximately 0.05 to approximately 5 percent by weight of the first skin therapeutic. The *Brassica olearacea italica* Seed Oil may be approximately 0.01 to approximately 10 percent by weight of the first skin therapeutic. For example, the first skin therapeutic may include less than approximately 1 percent by weight *Brassica olearacea italica* Seed Oil and greater than approximately 0.01 percent by weight of *Brassica olearacea italica* Seed Oil. In some implementations, the first skin therapeutic may include approximately the same amount or more bisabolol, by weight, than *Zingiber Officinales*. In some implementations, the first skin therapeutic may include sodium (C14-C16) olefin sulfonate. The first skin therapeutic may include approximately 0.1 to approximately 20 percent by weight of the sodium (C14-C16) olefin sulfonate.

The first skin therapeutic may include one or more additional compounds such as water, sodium PCA, glycerin, decyl glocoside, sodium cocoyl Isothionate, Disodium EDTA, PEG-7, Glyceryl Cocoate, Butylene Glycol, Lactic Acid, 1, 2, Hexanediol, Caprylyl Glycol, Benzalkonium Chloride, and/or a fragrance. For example, at least a portion of the remaining weight percentage (e.g., excluding the *Brassica* Olearacea *italica* Seed Oil, the bisabolol, and/or *Zingiber Officinales*) of the first skin therapeutic may include one or more the additional compounds in an appropriate amount. In some implementations, the additional compounds utilized in the first skin therapeutic may be based on the application method and/or the delivery form of the skin therapeutic (e.g., serum, balm, post-treatment, daily, etc.).

The first skin therapeutic may be in any appropriate delivery form, such as serum, cleanser, balm, etc. The first skin therapeutic may be utilized as a cleanser such that topical application of the first skin therapeutic (e.g., with or without water) may cleanse the skin. The cleanser may include a mild cleanser, such as, glycerin to cleanse skin, in some implementations.

In some implementations, the skin therapeutic may be a second skin therapeutic. The second skin therapeutic may include *Zingiber Officinales*, bisabolol (e.g., from German chamomile, *Matricaria recutita*, and/or *Myoporum crassifolium*), and *Brassica olearacea italica* Seed Extract. The second skin therapeutic may include approximately 5 percent to approximately 10 percent *Brassica olearacea italica* Seed Oil, approximately 0.025 percent to approximately 0.1 percent bisabolol, and approximately 0.025 percent to approximately 0.1 percent *Zingiber Officinales*. In some implementations, the second skin therapeutic may include more bisabolol than *Zingiber Officinales* by weight percentage. The second skin therapeutic may include hexyldecanol, cetylhydroxyproline palmitamide. For example, the second skin therapeutic may include approximately 2 to approximately 5 percent by weight of a combination of hexyldecanol, additional bisabolol, cetylhydroxyproline palmitide, stearic acid, and/or *Brassica campestirs* (Rapeseed) Sterols. The second skin therapeutic may include approximately 2 percent to approximately 5 percent by weight of witch hazel. The second skin therapeutic may include *Commiphora myrrha* resin extract. For example, the second skin therapeutic may include approximately 0.2-0.5 percent of *Commiphora myrrha* resin extract.

The second skin therapeutic may include one or more additional compounds. For example, the second skin therapeutic may include sunflower oil, sunflower seed oil, cyclopentasiloxane, *Simmondsia chinensis* seed oil, Squalane, Stearic Acid, Rapeseed oil (e.g., *Brassica campestirs* sterols), *Commiphora*, fragrances, and/or any other appropriate additional compound. For example, at least a portion of the remaining weight percentage (e.g., excluding the *Brassica olearacea italica* Seed Oil, the bisabolol, and/or *Zingiber Officinales*) of the second skin therapeutic may include one or more the additional compounds in an appropriate amount. In some implementations, the additional compounds utilized in the second skin therapeutic may be based on the application method and/or the delivery form of the skin therapeutic (e.g., serum, balm, post-treatment, daily, etc.).

The second skin therapeutic may include molecules and/or a total molecular weight under 500 Daltons. The second skin therapeutic may follow the Dalton 500 Rule to increase penetration (e.g., absorption) into the skin. In some implementations, the second skin therapeutic may be oil based and/or not include water to penetrate the stratum corneum.

The second skin therapeutic may be in any appropriate delivery form, such as serum, cleanser, balm, etc. For example, the second skin therapeutic may be utilized as a post treatment balm. The balm may be applied topically to the skin after medial procedures, cosmetic procedures, after damage to the skin, and/or to inhibit and/or reduce damage to the skin. For example, the balm may be applied to the skin after microderm abrasion, laser resurfacing, surgical procedures (e.g., reconstruction surgeries, liposuction, etc.), liquid nitrogen procedures, micro-needling, Levulan® procedures, Efudex® procedures, and/or any other procedure that may damage skin. The balm may be applied to the skin after minor cuts, irritations, itchiness, folliculitis, insect bites, burns, dry skin, etc. The post treatment balm may soothe skin, reduce redness, reduce inflammation, and/or reduce recovery time (e.g., by promoting healing), in some implementations. The second skin therapeutic may not include water in some implementations to inhibit irritation to post-treatment skin.

In some implementations, the skin therapeutic may be a third skin therapeutic. The third skin therapeutic may include *Zingiber Officinales*, bisabolol, and *Brassica olearacea italica* Seed Extract. The third skin therapeutic may include approximately 5 percent to approximately 10 percent *Brassica olearacea italica* Seed Oil, approximately 0.025 percent to approximately 0.1 percent bisabolol, and approximately 0.025 percent to approximately 0.1 percent *Zingiber Officinales*. In some implementations, the third skin therapeutic may include more bisabolol than *Zingiber Officinales* by weight percentage. The third skin therapeutic may include approximately 0.1 to approximately 10 percent of *Simmondsia chinensis* Seed Oil (Jojoba) and/or Lanolin. The Third Skin Therapeutic May include hexyldecanol, cetylhydroxyproline palmitamide. For example, the third skin therapeutic may include approximately 3 to approximately 3.5 percent by weight of a combination of hexyldecanol, additional bisabolol, cetylhydroxyproline palmitide, stearic acid, and/or *Brassica campestirs* (Rapeseed) Sterols. The third skin therapeutic may include approximately 3 to approximately 3.5 percent by weight of witch hazel, in some implementations. The third skin therapeutic may include sunflower seed oil and/or a fragrance such as spearmint oil (e.g., Mentha Virisdis Leaf Oil). For example, the third skin therapeutic may include approximately 3-5 percent of sunflower seed oil and/or less than 5 percent spearmint oil.

The third skin therapeutic may include one or more additional compounds. For example, the third skin therapeutic may include beeswax, butyrospermum, Parkii, Caprylic Capric Triglyceride, cetyl palmitate, mineral oil, petrolatum, squalane, menthol, menthyl lactate, tocopheryl acetate, and/or any other appropriate additional compound. For example, at least a portion of the remaining weight percentage (e.g., excluding the *Brassica olearacea italica* Seed Oil, the bisabolol, and/or *Zingiber Officinales*) of the third skin therapeutic may include one or more the additional compounds in an appropriate amount. In some implementations, the additional compounds utilized in the third skin therapeutic may be based on the application method and/or the delivery form of the skin therapeutic (e.g., serum, balm, post-treatment, daily, etc.).

The third skin therapeutic may be in any appropriate delivery form, such as serum, cleanser, balm, etc. For example, the third skin therapeutic may be utilized as a lip balm, in some implementations.

In some implementations, the skin therapeutic may be a fourth skin therapeutic. The fourth skin therapeutic may include *Zingiber Officinales*, bisabolol, and *Brassica olearacea italica* Seed Extract. The fourth skin therapeutic may include approximately 5 percent to approximately 10 percent *Brassica olearacea italica* Seed Oil, approximately 0.025 percent to approximately 0.1 percent bisabolol, and approximately 0.025 percent to approximately 0.1 percent *Zingiber Officinales*. In some implementations, the fourth skin therapeutic may include more bisabolol than *Zingiber Officinales* by weight percentage. The fourth skin therapeutic may include hexyldecanol, cetylhydroxyproline palmitamide. The fourth skin therapeutic may include approximately 3 to approximately 5 percent by weight of witch hazel. The fourth skin therapeutic may include approximately 3 to approximately 5 percent by weight of a combination of hexyldecanol, additional bisabolol, cetylhydroxyproline palmitide, stearic acid, and/or *Brassica campestirs* (Rapeseed) Sterols. The fourth skin therapeutic may include silver (e.g., any appropriate form of silver). The silver may be approximately 0.1 to approximately 0.5 percent of the third skin therapeutic by weight. The fourth skin therapeutic may include sunflower oil (e.g., *Helianthus annuus* seed oil). The fourth skin therapeutic may include approximately 4 to approximately 6 percent by weight of sunflower oil. The fourth skin therapeutic may include oat and/or chamomile. The fourth skin therapeutic may include water, glycerin, and oat (e.g., *Avena sativa* extract), in some implementations (e.g., approximately 3.5 to approximately 5 percent by weight). The fourth skin therapeutic may include aloe (e.g., approximately 1 to approximately 5 percent by weight) and/or a soothing compound (e.g., approximately 1-approximately 5 percent by weight). For example, a soothing compound may include trideceth-9, PEG-5 isononanoate and/or water.

The fourth skin therapeutic may include one or more additional compounds. For example, the fourth skin therapeutic may include Sodium PCA, Dimethyl Isosorbide, Glycerin, Cetearyl Alcohol/Ceteareth-20, Glyceryl Stearate/PEG-100 Steararte, Stearic Acid, Squalane, Butyrospermum Parkii Butter, Caprylic/Capric Triglyceride, Cetyl Alcohol, Isohexadecane, Dimethicone, Cyclomethicone, *Brassica Campestris* Sterols, Acid, *Echinacea* Purpura Extract, water, Dimethyulacrylamide/Acrylic Acid/Polystyrene Ethyl Methacrylate Copolymer, *Oryza Sativa* Bran Extract, Phenoxyethanol, Sodium Benzoate, Aqua, Glycerin, Beta-Glucan, PEG-8, Aqua, *Piper Methysticum*, PEG-8/SMDI Copolymer, Benzyl Alcohol, Methylchloroisothiazolinone, Methylisothiazolinone, Epilobium *Angustifolium* Flower/Leaf/Stem Extract, Fragrance, Polyacrylamide, C13-14 Isoparaffin, PEG-7 Laurate, and/or any other appropriate additional compound. For example, at least a portion of the remaining weight percentage (e.g., excluding the *Brassica olearacea italica* Seed Oil, the bisabolol, and/or *Zingiber Officinales*) of the fourth skin therapeutic may include one or more the additional compounds in an appropriate amount. In some implementations, the additional compounds utilized in the fourth skin therapeutic may be based on the application method and/or the delivery form of the skin therapeutic (e.g., serum, balm, post-treatment, daily, etc.).

The fourth skin therapeutic may be in any appropriate delivery form, such as serum, cleanser, balm, etc. For example, the fourth skin therapeutic may be utilized as a soothing cream, in some implementations.

In some implementations, the skin therapeutic may be a fifth skin therapeutic. The fifth skin therapeutic may include *Zingiber Officinales*, bisabolol, and *Brassica olearacea italica* Seed Extract. The fifth skin therapeutic may include approximately 5 percent to approximately 10 percent *Brassica olearacea italica* Seed Oil, approximately 0.025 percent to approximately 0.1 percent bisabolol, and approximately 0.025 percent to approximately 0.1 percent *Zingiber Officinales*. In some implementations, the fifth skin therapeutic may include more bisabolol than *Zingiber Officinales* by weight percentage. The fifth skin therapeutic may include hexyldecanol, cetylhydroxyproline palmitamide. For example, the fifth skin therapeutic may include approximately 0.02 to approximately 1 percent by weight of bisabolol and/or approximately 0.2 to approximately 1 percent by weight of *Zingiber Officinales*. The fifth skin therapeutic may include approximately 0.05 to approximately 2 percent by weight of clove oil. The fifth skin therapeutic may include sunflower seed oil, a wax (e.g., sunflower wax and/or a mixture of glyceryl debehenate, tribehenin, and/or glyceryl behenate), sulforaphane, and/or raspberry extract. For example, the fifth skin therapeutic may include approximately 10 percent of a wax (e.g., a mixture of glyceryl debehenate, tribehenin, and/or glyceryl behenate) and/or sunflower wax. The fourth skin therapeutic may include approximately 4 to approximately 6 percent by weight of sunflower oil and/or approximately 1 to approximately 4 percent by weight of sulforaphane. The fifth skin therapeutic may include a retinol, such as retinyl palmitate and/or retinoic acid (e.g., approximately 2 to approximately 4 percent by weight).

The fifth skin therapeutic may include one or more additional compounds. For example, the fifth skin therapeutic may include Cyclopentasiloxane, *Helianthus Annuus* Seed Oil, Squalane, Retinyl Palmitate, Dimethyl Isosorbide, Hydroxypinacolone, Stearic Acid, *Brassica campestirs* (Rapeseed) Sterols, Fragrance, and/or any other appropriate additional compound. For example, at least a portion of the remaining weight percentage (e.g., excluding the *Brassica olearacea italica* Seed Oil, the bisabolol, and/or *Zingiber Officinales*) of the fifth skin therapeutic may include one or more the additional compounds in an appropriate amount. In some implementations, the additional compounds utilized in the fifth skin therapeutic may be based on the application method and/or the delivery form of the skin therapeutic (e.g., serum, balm, post-treatment, daily, etc.).

The fifth skin therapeutic may be in any appropriate delivery form, such as serum, cleanser, balm, etc. For example, the fifth skin therapeutic may be utilized as a night repair serum, in some implementations.

In some implementations, the skin therapeutic may be a sixth skin therapeutic. The sixth skin therapeutic may include *Zingiber Officinales*, bisabolol, and *Brassica olearacea italica* Seed Extract. The sixth skin therapeutic may include approximately 5 percent to approximately 10 percent *Brassica olearacea italica* Seed Oil, approximately 0.025 percent to approximately 0.1 percent bisabolol, and approximately 0.025 percent to approximately 0.1 percent *Zingiber Officinales*. In some implementations, the sixth skin therapeutic may include more bisabolol than *Zingiber Officinales* by weight percentage. The sixth skin therapeutic may include hexyldecanol, cetylhydroxyproline palmitamide. For example, the fifth skin therapeutic may include approximately 0.02 to approximately 1 percent by weight of bisabolol and/or approximately 0.2 to approximately 1 percent by weight of *Zingiber Officinales*. The fifth skin therapeutic may include approximately 0.05 to approximately 2 percent by weight of clove oil. The sixth skin therapeutic may include sunflower oil (e.g., approximately 9 to approximately 11 percent by weight. The sixth skin therapeutic may include approximately 6 to approximately 8 percent of tetrahexyl ascorbate and/or vitamin C in some implementations.

The sixth skin therapeutic may include one or more additional compounds. For example, the sixth skin therapeutic may include Glyceryl Behenate, *Helianthus Annuus* Seed Oil, Cyclopentasiloxane, *Simmondsia Chinensis* Seed Oil, Dimethicone, Squalane, Stearic Acid, *Brassica campestirs* (Rapeseed) Sterols, Polymethylsilsesquioxane, Fragrance, and/or any other appropriate additional compound. For example, at least a portion of the remaining weight percentage (e.g., excluding the *Brassica* Olearacea *italica* Seed Oil, the bisabolol, and/or *Zingiber Officinales*) of the sixth skin therapeutic may include one or more the additional compounds in an appropriate amount. In some implementations, the additional compounds utilized in the sixth skin therapeutic may be based on the application method and/or the delivery form of the skin therapeutic (e.g., serum, balm, post-treatment, daily, etc.).

The sixth skin therapeutic may be in any appropriate delivery form, such as serum, cleanser, balm, etc. For example, the sixth skin therapeutic may be utilized as a daily regenerating serum, in some implementations.

The skin therapeutic composition may reduce inflammation. In some implementations, users satisfaction may be increased by using the skin therapeutic composition that includes natural products rather than traditional anti-inflammatory compounds such as corticosteroids and/or immunosuppressive drugs (e.g., which may prolong healing time due to the immunosuppressive effect). The use of the compositions in the described skin therapeutic composition may increase user satisfaction over other natural anti-inflammatory compounds such as 4-propyl guaiacol, curcumin, luteolin, C ferulic acid, gernistein, and epigallocatechin gallate, which may cause skin discoloration and/or have overpowering scents (e.g., which may discourage use). Decreases in skin inflammation are not generally considered additive and addition of multiple topical products to reduce inflammation does not generally substantially increase the inflammation. However, the skin therapeutic composition (e.g., first-sixth skin therapeutic composition) may unexpectedly decrease inflammation more than the components of the skin composition. The skin therapeutic composition may not discolor skin upon application. For example, fragile skin (e.g., post treatment skin, burned skin, etc.) may be prone to skin discoloration and the skin therapeutic composition may not discolor the skin upon application.

In various implementations, application of the skin therapeutic composition may provide analgesic effect and/or anti-histamine effect. The application of the skin therapeutic composition may stimulate anti-aging genes including stimulating production of hyaluronic acid, collagen, and/or elastin. The application of the skin therapeutic composition may inhibit production of inflammatory agents, such as cytokines, chemokines, and/or hormones (e.g., PGE-e) produced by keratinocytes, fibroblasts, and immune cells. A user may have inflamed skin due to underlying conditions and/or skin treatments and application of the skin therapeutic composition may reduce the inflammation (e.g., more quickly than without application). As illustrated in FIG. 1, PGE-2 levels after laser treatment causes long-term inflammation and stimulation of PGE-2. (Although inflammation is an integral component of wound healing, excessive inflammation has been linked to abnormal wound healing outcomes, specifically fibrosis and scar formation. Laser induces a 9 fold increase in PGE-2 and even at 21 days post laser, levels are 4× control. See Sandulache, V. C. et al., Al ArchOtolaryngol Head and Neck Surg. 2007; 133:365-374)._Long-term inflammation may further damage skin by causing abnormal healing outcomes, such as scarring and/or discoloration, and may decrease user satisfaction with the skin treatment (e.g., since skin may appear inflamed and/or be sensitive due to inflammation). In some implementations, laser treatments may cause inflammation (e.g., as measured by prolonged elevated levels of PGE-w and/or IL-1) even approximately 20 days after treatment. Thus, application of the skin therapeutic composition after treatments, such as laser treatments, may improve healing outcomes (e.g., by reducing inflammation) and/or by increasing user satisfaction with the skin treatment.

In some implementations, the application of the skin therapeutic composition may reduce the severity of diseases such as rosacea, eczema, and acne. The application of the skin therapeutic composition may decrease dryness (e.g., dry skin, cracked skin, and/or normal dry skin). The application of the skin therapeutic composition may improve skin damaged by treatments such as medical treatments (e.g., surgical procedures, ablative treatments, etc.) and/or non-medical treatments (e.g., chemical peels, injectables, etc.).

In various implementations, although one or more of the ingredients in the skin therapeutic composition may have anti-inflammatory properties, the combination of the ingredients as described produces unexpectedly greater anti-inflammatory benefits than an additive benefit. In some implementations, the combination of ingredients may act in a surprising way due to the unexpected benefit (e.g., improved appearance of skin and/or decreased healing time) of concurrently reducing inflammation, reducing redness, applying an analgesic, providing an antihistamine by application of the skin therapeutic composition. In some implementations, the ability of one or more of the skin compositions to reduce two or more of inflammation, redness, dryness, scarring, discoloration, and/or histamine production may promote healing and/or reduce healing time more quickly than each component of the skin composition(s) alone. For example, since factors such as redness, inflammation, dryness, scarring, etc. may be related, as multiple factors are decreased the overall healing time may be decreased substantially more than expected based on the individual properties of the components.

A study was performed in which redness & inflammation and the recovery and rebuilding phase of skin healing was examined in a population in which the Post Treatment Balm was and was not administered. A reduction in healing time caused by application of the skin therapeutic composition occurred. With the Post Treatment Balm application, redness and inflammation has a shortened time period. Redness and inflammation may be reduced and/or eliminated in approximately half to approximately one quarter of the amount of time with the application of the skin therapeutic composition. In the study, even on Day 1 redness and inflammation was less when the Post Treatment Balm was administered than when the Post Treatment Balm was not administered. By Day 4, redness and inflammation almost is eliminated in the population in which the Post Treatment Balm was applied as opposed to the population in which the Post Treatment Balm was not applied Healing and recovery was also increased. The Recovery and Rebuilding phase begins earlier in the population in which the Post Treatment Balm was administered. Without the Post Treatment Balm the Rebuilding Phase is delayed until Inflammation ends around Day 16, which is typical without blocking inflammatory mediators. The Recovery/Repair period in the population in which the Post Treatment Balm was administered may begin 4 or more days earlier than in the population in which the Post Treatment Balm was not administered. By decreasing the inflammation time and beginning the recovery/repair period more quickly, outcomes from treatments may be improved and the likelihood of skin damage (e.g., pigmentation and/or scarring) due to pro-longed inflammation after treatment may be decreased. User satisfaction may be increased by reducing the down time associated with skin treatments and/or improved outcomes.

In various implementations, an effective amount of skin therapeutic composition(s) may be administered to a user to reduce inflammation (e.g., when compared with inflammation without administration of the skin therapeutic composition). An effective amount of skin therapeutic composition(s) may be administered to reduce redness, dryness, cracking, pain, and/or flaking of the skin. In some implementations, an effective amount of skin therapeutic composition(s) may be administered to inhibit prolonged inflammation due to skin treatments. An effective amount of skin therapeutic composition(s) may be administered to a user to reduce healing time and/or speed entry of skin into a recovery phase. The skin therapeutic composition may be administered to a user by topically applying the skin therapeutic composition to at least a portion of a user's skin. The skin therapeutic composition(s) may be applied single and/or in combination. The skin therapeutic compositions may be administered periodically (e.g., daily) and/or as desired (e.g., by a user to soothe skin) over at least a period of time (e.g., a week, a month, etc.). In some implementations, a treatment regimen may be performed by an individual based on the individual's skin condition (e.g., dry, post-treatment, burn, etc.).

The skin therapeutic composition may have a low molecular weight (e.g., molecular weight of less than 500 Daltons) with oil solubility properties to facilitate penetration in skin.

In some implementations, the described skin therapeutic composition (e.g., first skin therapeutic composition, second skin therapeutic composition, third skin therapeutic composition, fourth skin therapeutic composition, fifth skin therapeutic composition, sixth skin therapeutic composition, and/or other described skin therapeutic compositions) may be utilized in various administration forms. For example, the skin therapeutic composition may be included in a Dermal Repair Night Cream. The dermal repair night cream may be used for overnight anti aging moisturization and/or to help with the appearance of severely dry, aged, and dehydrated skin.

The skin therapeutic composition may be included in a Neck Firming Cream. The neck firming cream may be used with a variety of skin types and/or ages. The neck firming cream may improve slack skin in the neck area, improve the gradual gravitational decline due to age, and/or help promote skin elasticity.

The skin therapeutic composition may be included in a Light N Bright Cream. The cream may have a velvety feel. The cream may lighten hyper-pigmentation, dark spots and/or melasma. Application of the cream may leave uneven skin tone lighter, brighter, and/or more luminous.

The skin therapeutic composition may be included in a Pure Radiance Oxygen Mist. The mist may be an invigorating and/or refreshing mist. The mist may complete the cleansing process and/or re-establishing correct hydration while revitalizing skin tissue. The mist may be used daily, for example, on a variety of skin types.

The skin therapeutic composition may be included in a Silver Relief Lotion. The lotion may calm and/or soothe red, blotchy, sensitive skin, and/or replenish lost oils.

The skin therapeutic composition may be included in a Sun Protector Drops. The drops may include titanium. The drops may provide skin with the broadband protection of Titanium Dioxide to inhibit harmful damage caused by exposure to the sun's UVA and UVB rays. The drop may be safe and gentle. The drops may include a purified form of titanium dioxide and/or purified water to reduce the risk of allergic reactions. The drops may be added to other creams, lotions, and/or makeup to provide added protection, as desired, in some implementations (e.g., allowing for a custom application of sun protection).

The skin therapeutic composition may be included in a Luxe SunSilk with a SPF protection (e.g., SPF 50). The sunscreen may provide broad spectrum UVA and UVB sunscreen for a variety of skin types (e.g., dry and/or oily skin types). The sunscreen may have a light weight texture with a fresh and soft sensory feel.

The skin therapeutic composition may be included in a Derma Clear Pore Refining Mask. The mask may be a zinc and sulfur-based corrective treatment for oily, pore clogged and/or problematic skin. The mask may have a thick creamy texture and/or may leaves the skin calm and refreshed. The mask may have a dynamic blend of super effective ingredients selected to purify the skin, exfoliate, remove excess oil, cleanse pores, and/or reduce comedones.

The skin therapeutic composition may be included in a Derma Bright Oxygen Mask. The mask may be a fresh light weight, anti aging mask. The mask may give the skin a soft velvety feel. The mask may reduce hyper-pigmentation and leave uneven skin with a more luminous skin tone. The mask may be utilized to lighten dark spots, age spots, and/or Melasma.

The skin therapeutic composition may be included in a Derma Clear-Pore Refining Mask. The mask may include a zinc and sulfur-based corrective treatment for oily, pore clogged and/or problematic skin. The mask may have a thick creamy texture that leaves the skin calm and refreshed. The mask may include a dynamic blend of super-effective ingredients designed to purify the skin, exfoliate, remove excess oil, cleanse pores and/or reduce comedones.

The skin therapeutic composition may be included in a Rapid Wrinkle Releaser Mask. The mask may include retinol. The mask may restore a more youthful suppleness and/or radiance with as little as single application of this vitality-enhancing mask. The advanced antioxidant formula in the mask may include a concentrated Retinol, anti inflammatory compound, and/or anti-photo wrinkle compound to assist in pigment and UV filter deposition.

The skin therapeutic composition may be included in a Wrinkle Filler. The filler may be a cream that is an illusionary cream that fills in the gaps in the skin to perform a real life wrinkle vanishing act.

The skin therapeutic composition may be included in an Eye Lift. The skin around the eye is extremely delicate and much more sensitive to environmental stresses such as sun and pollution. Environmental factors directly and/or indirectly cause breaks in the skins matrix. Fine lines and wrinkles show signs of dehydration and age. Dark circles and puffiness can give the appearance of being tired or stressed. The Eye lift cream may counteract these stresses on the skin around the eye.

The skin therapeutic composition may be included in a Hand Plumping Lotion. The lotion may be topical applied to the hands and/or other parts of the body. The lotion may be optimized for comfort (e.g., the texture and thickness). The lotion may deliver astonishing actives in a moisturizing and nourishing lotion.

The skin therapeutic composition may be included in an Instant Face Tightening product. The product may be designed to provide approximately immediate lifting and/or tightening effects to the skin. In just moments after application, you'll experience younger looking skin. The product appears to diminish fine lines and wrinkles as well as tightens and firms.

In some implementations, the skin therapeutic composition may include *Brassica olearacea italica* Seed Oil and at least one of bisabolol or *Zingiber Officinales*. The skin therapeutic composition may include *Brassica olearacea italica* Seed Oil, bisabolol, and *Zingiber Officinales*. The combination of the components in the skin therapeutic composition may have a greater effect on skin health and/or appearance than merely the additive effect of the components. Unlike the components used singularly, the skin therapeutic composition decreases redness, soothes skin (e.g., as determined by user), reduces inflammation, and/or reduces recovery time upon administration. For example, one or more of the described skin therapeutic composition may be administered to the skin of a user on an administration schedule. When more than one skin therapeutic compositions is administered, the skin therapeutic compositions may be administered sequentially and/or concurrently. The skin therapeutic composition(s) may be administered periodically and/or as desired by the user. Since the skin therapeutic composition has non-irritating components, the skin therapeutic composition may be applied up to 10 times a day, in some implementations. The skin therapeutic composition may reduce redness and/or inflammation as soon as immediately after application. The skin therapeutic composition reduction of inflammation may promote healing (e.g., by allowing the skin's natural healing processes to begin rather than waiting for inflammation to naturally occur, which may be up to 2 weeks later after some treatments).

In various implementations, the skin therapeutic composition (e.g., first-sixth skin therapeutic composition, other described compositions, and/or combinations thereof) may be utilized to treat conditions and/or to promote healthy skin. For example, the skin therapeutic composition(s) may be utilized as daily regimen and/or anti-aging regimen. The regimen may include a day (e.g., sixth skin therapeutic composition) and/or a night serum (e.g., fifth skin therapeutic composition). For example, the day serum may be applied in approximately the morning time and/or the night serum may be applied in approximately the night time. In some implementations, the skin may be cleansed (e.g., with any appropriate cleanser such as a cleanser that includes the first skin therapeutic composition) prior to applying the day and/or night serum. The day and/or night serum may be gently applied to skin (e.g., face, neck, hands, etc.). The day and/or night serum may be allowed to be at least partially absorbed prior to application of other products (e.g., creams, makeup, sunscreen, etc.). In some implementations, if the day and/or night serum includes retinol, the regimen may inhibit application for at least two weeks after some medical procedures (e.g., microderm abrasion, microneedling, laser treatments, etc.) and/or skin conditions (e.g., burns). Topical application of the day and night serum may provide more glowing, healthy, and/or youthful appearance in days.

In some implementations, the skin therapeutic composition(s) may be utilized to treat dry skin. For example, a dry skin treatment regimen may include application of dry skin treatment products such as a balm including first skin therapeutic composition, a cleanser including a second skin therapeutic composition, a soothing cream including fourth skin therapeutic composition, a lip balm including a third skin therapeutic composition, and/or other skin therapeutic compositions. In some implementations, the balm may be applied to the skin and allowed to at least partially absorbed before applying the soothing cream. In some implementations, the soothing cream may be applied to areas in need to extra hydration, extra dryness, and/or extra irritation (e.g., as opposed to other areas of the individual's skin with less irritation). The lip balm may be applied to the lips, based on user preference and/or if the individual's lips are dry (e.g., after treatment with the balm and/or in place of treatment with the balm). In some implementations, the area of skin to which the balm is applied may be cleansed prior to application with a cleanser, such as a cleanser that includes second skin therapeutic composition. Topical application of the dry skin treatment products may seal the skin against water loss, promote repair to the damaged skin barrier, and/or interrupt the inflammatory response triggered by the dry skin. The use of two or more of the dry skin treatment products may provide a chain reaction of effects (e.g., reduce inflammation, reduce inflammatory response, seal skin, promote repair, etc.) that magnify the effects of the dry skin treatment products on the skin (e.g., as opposed to when just a component of one of the skin therapeutic compositions is used individually).

In some implementations, the skin therapeutic composition(s) may be utilized to treat, sooth, and/or promote repair of burns (e.g., caused by treatments, such as laser treatments, and/or accidental burns). For example, a balm including the first skin therapeutic composition may be applied to burns immediately after a burn has occurred and/or a period of time after a burn has occurred (e.g., a few days after a burn has occurred). The application of the balm proximate in time to the burn occurring may reduce the severity of the burn (e.g., second degree burn to first degree burn). The application of the balm may promote healing and/or sooth burned skin. For example, a second degree burn may be healed in less than 3 days (e.g., since healing of the burn may begin more quickly than without application of the balm). The balm may be applied once a day, twice a day, and/or as desired by the user.

In some implementations, the skin therapeutic composition(s) may be utilized to reduce scarring. For example, a balm including the first skin therapeutic composition may be applied to scars to reduce additional scarring and/or promote healing of the scarring.

In some implementations, the skin therapeutic composition(s) may be utilized in a regiment for post medical (e.g., surgical and/or nonsurgical) and/or cosmetic skin procedures. For example, the post-treatment regimen may follow laser treatments, tattoo removal, microneedling, and/or other procedures. The skin therapeutic composition(s) may be applied according to a post treatment regimen. The post treatment regimen may include products such as a balm that includes first skin treatment composition, soothing cream including fourth skin treatment composition, cleanser including second skin treatment composition, and/or other skin treatment compositions. The regimen may include allowing application of the balm (e.g., up to six times a day) and restricting application of skin treatment composition and/or other topical skin products for 24 hours after the procedure. The balm may be applied for at least a week, in some implementations. In some implementations, the balm and/or cool compresses may be applied as needed to sooth the post-treatment skin. The soothing cream may be applied more than once a day once the 24 hour treatment period has lapsed during the post-treatment regimen. The balm may be allowed to at least partially absorb into the skin prior to application of the soothing cream. The cleanser may be utilized (e.g., after the first 24 hours, 48 hours, and/or other procedure recommended period) one to two times daily on the area (e.g., treatment area) and/or may be applied for at least a week. In some implementations, a daily serum (e.g., including the sixth skin treatment composition) may be applied at least 72 hours after the treatment in the evenings. The post treatment regimen may accelerate recovery in as little as 4 days after treatments such as ablative laser treatments, chemical peels, in-office procedures (e.g., breast, facial, and/or liposuction, liquid nitrogen procedures, etc.), Levulan®, Efudex®, etc.

The skin therapeutic composition(s) may be applied according to the post treatment regimen for recovery from a tattoo removal, in some implementations. The post treatment regimen may include products such as a balm that includes first skin treatment composition cleanser including second skin treatment composition, and/or other skin treatment compositions. In some implementations, the post treatment regimen may or may not include a soothing cream including the fourth skin therapeutic composition. For example, rather than applying Aquaphor® (e.g., a standard post-treatment application), the balm including the first skin therapeutic composition may be applied to the area of the tattoo removal. The cleanser may be applied to the skin as early as 24 hours after the procedure during the treatment regimen and/or the daily serum including the sixth skin treatment composition may be applied (e.g., in addition to and/or in place of the balm) as early as 72 hours after the procedure. The balm, cleanser, and/or daily serum may be applied daily (e.g., once, twice, and/or more times a day) for at least two weeks to promote healing and/or reduce scarring. The balm may have analgesic properties that may reduce pain associated with the tattoo removal treatment. Application of the tattoo removal treatment regimen may decrease healing time and/or improve skin feel and/or comfort (e.g., less tight, hot, and/or dry). In some implementations, the balm may seal the skin from contacting air, which can increase, and individual's discomfort post-tattoo removal treatment.

In some implementations, the skin treatment composition(s) may be applied in a pre-treatment regimen. For example, prior to some procedures, such as micro-needling, application of one or more of the skin treatment compositions may reduce irritation, decrease discomfort, reduce redness, and/or reduce inflammation. The pre-treatment regimen may include applying a daily serum including the sixth skin treatment composition prior to the procedure, such as microneedling. In some implementations, a cleanser including the second skin treatment composition may be applied prior to applying the daily serum in the pre-treatment regimen. The skin may be patted dry prior to application of the daily serum. In some implementations, the balm including the first skin treatment composition may be applied after the microneedling procedure and/or at least a portion of the post-treatment procedure may be administered.

In some implementations, one or more kits may be created that include one or more of the skin therapeutics (e.g., first-sixth skin therapeutic and/or other described skin therapeutics). A kit may be associated with an administration regimen. For example, a first kit may be created that includes one or more skin therapeutics for a first condition (e.g., dry skin, post-treatment, anti-aging, burn, etc.). The first kit may include formulation(s) (e.g., serum, cream, balm, cleanser, etc.) of one or more of the skin therapeutic compositions (e.g., first-sixth skin therapeutic composition and/or other described skin therapeutics) that are administered to a user during a first administration regimen (e.g., dry skin, anti-aging, burns, cuts, post-treatment, etc.). The first administration regimen may be followed by a user, who uses one or more of the products in the first kit at least partially based on the provided administration regimen. In some implementations, the kits may be an add-on kit for supplementing another kit. For example, a post-treatment add on kit may include skin therapeutics that are not found in one or more other kits (e.g., such that two or more kits can be used to follow an administration regimen while leveraging use of an existing kit the user may already have or may need larger quantities). For example, a post treatment kit may include one or more skin therapeutics that are administered according to the post-treatment regimen. The post-treatment kit may include: a balm (e.g., including the first skin treatment regimen), a cleanser (e.g., including the second skin treatment composition), and/or other formulations of the skin treatment compositions (e.g., soothing cream, daily serum, etc.). As another example, a post treatment add on kit may be created for user of a daily kit (e.g., daily serum, cleanser, and/or night serum) such that a user may follow the post-treatment regimen (e.g., which may include daily serum, balm and cleanser) using one or more products in the daily kit in addition to the add on post-treatment kit (e.g., balm).

EXAMPLES

Example 1

A skin therapeutic, Skin Therapeutic Composition 1, was prepared by mixing approximately 0.025 percent to approximately 0.1 percent by weight of *Zingiber Officinales*, approximately 0.25 percent to approximately 0.1 percent be weight of Bisabolol, and approximately 0.05 percent of *Brassica olearacea italica* Seed Oil. The Skin Therapeutic Composition 1 also included approximately 7 percent by weight of Sodium C-14-16 olefin sulfonate. One or more additional ingredients were included in the Skin Therapeutic Composition 1.

The Skin Therapeutic Composition 1 may be applied (e.g., topically) to the skin on a periodic basis and/or as desired by the user.

Example 2

A Cleanser was created using the Skin Therapeutic Composition 1, prepared in Example 1. The Cleanser may not include harsh surfactants such as lauryl or lauryl sulfate (e.g., to inhibit skin irritation due to harsh surfactants). The Cleanser may include gentle surfactants and antioxidants.

The Cleanser may be applied (e.g., topically) to the skin (e.g., face and/or body) of a user. The Cleanser may be pH balanced. The Cleanser may be suitable for all skin types (e.g., including post treatment once cleansing is allowed). The Cleanser may be non-sensitizing and/or anti-inflammatory. The Cleanser may be gentle to inhibit substantial stripping of nutrients from the skin during application. The Cleanser may be soothing and/or refreshing. The Cleanser may remove daily pollutants, dirt, and/or make-up. Use of the product may leave a protective barrier on the skin. The Cleanser may suppress production (e.g., growth) of harmful microbes.

The Cleanser may be applied daily, twice a day, and/or as appropriate (e.g., based on user preferences, treatment regimens, etc.). A user may apply water (e.g., warm water) to the area to be cleansed, such as the face and/or body. The Cleanser may be applied to the hands and lathered prior to application on the area to be cleansed. In some implementations, the cleanser may be applied to the area to be cleansed and gently rubbed or stroked (e.g., in a circular motion), for example, to allow the cleanser to lather on the area to be cleansed. The area to be cleansed may be rinsed with water (e.g., warm water) to remove the Cleanser from the skin and patted approximately dry with a towel. Application of the Cleanser according to the administration schedule may sooth the skin of the user. Application of the cleanser may promote healing by keeping the area to be cleansed clean (e.g., by removing makeup, fluids leaching from the skin, daily pollutants, etc.).

In some implementations, the Cleanser may be utilized as a cleanser. A user may apply the cleanser on any appropriate portion of the user's body. An area of the skin (e.g., face) may be moistened (e.g., with water) prior to administration of Cleanser. The cleanser may be dispensed into moistened hands and the cleanser may be allowed to lather (e.g., by rubbing hands together). The lathered cleanser, that includes Skin Therapeutic 1, may be applied to the portion of the body (e.g., face). The lathered cleanser may be applied with a circular motion, in some implementations. The applied cleanser may be rinsed off the part of the body with water. The cleansed part of the body may be patted dry (e.g., to inhibit irritation of the skin by rubbing). The cleanser may be reapplied, in some implementations (e.g., to remove makeup left behind after a previous cleansing). In some implementations, the Cleanser may be applied daily (e.g., mornings, nightly, and/or other times during the day).

In some implementations, administration of the Skin Therapeutic 1 as a cleanser may sooth damaged skin (e.g., when compared to other cleansers such as soap). The cleanser may be pH balanced such that it is suitable for use on a specific portion of the body (e.g., face). The cleanser may provide anti-inflammatory benefits to skin or areas proximate to the skin on which the cleanser is applied.

The Skin Therapeutic 1 Cleanser may be mild and effective (e.g., capable of cleansing skin). The Cleanser may sooth skin and/or reduce the appearance of fine wrinkles. The Cleanser may not include lauryl and/or laureth sulfates (e.g., commonly used to produce effective cleansers but may cause skin irritation and/or drying), in some implementations. The Cleanser may be capable of removing makeup and/or residue on skin from pollutants to which the skin is exposed (e.g., in the air). The Cleanser may not damage the protective barrier of the skin. In some implementations, the Skin Therapeutic Cleanser may inhibit growth and/or suppress growth of harmful microbes while being gentle on skin (e.g., not substantially stripping nutrients from skin). The Skin Cleanser may be "soap-free".

Example 3

A skin therapeutic, Skin Therapeutic Composition 2, was prepared by mixing approximately 0.025 percent to approximately 0.1 percent *Zingiber Officinales*, at least 0.025 bisabolol (e.g., from German chamomile, *Matricaria recutita*, and/or *Myoporum crassifolium*), and approximately 7 percent by weight of *Brassica olearacea italica* Seed Extract. The amount of bisabolol may be greater than the amount of *Zingiber Officinales* included in the Skin Therapeutic Composition 2. For example, the Skin Therapeutic Composition 2 may include up to approximately 70 percent more bisabolol than *Zingiber Officinales*, in some implementations. The Skin Therapeutic Composition 2 may include approximately 15 percent by weight of sunflower oil and/or a mixture of glycerl debehenate, tribehenin, and/or glyceryl behenate. The Skin Therapeutic Composition 2 may include approximately 0.4 percent by weight of menthol and/or *Commiphora myrrha* resin extract. The Skin Therapeutic may include approximately 4 percent of witch hazel and/or a combination of hexyldecanol, bisabolol, cetylhydroxyproline palmitide, stearic acid, and/or *Brassica campestirs* (Rapeseed) sterols.

Since the mixture includes a plurality of oils, homogeneity of the mixture may be difficult to achieve. Thus, the ability to emulsify the mixture is an unexpected result. User satisfaction may be increased by providing Skin Therapeutic Compound 2 as an approximately homogenous mixture since use may be facilitated (e.g., premixing before application may not be performed, approximately even application may be easier with a homogenous mixture, etc.). Skin Therapeutic Compound 2 may be more effective when homogenous (e.g., when compared with other skin care products and/or non-homogenous skin care products) since delivery of the compounds in the mixture may be more evenly applied.

The Skin Therapeutic Composition 2 may be applied (e.g., topically) to the skin on a periodic basis and/or as desired by the user.

Example 4

A post-treatment balm may be prepared including the Skin Therapeutic Composition 2. The Skin therapeutic composition 1 and/or 2 may be used in place of Aquaphor® to improve outcomes (e.g., improve recovery times and/or decrease down time).

The Skin therapeutic composition 2 may be utilized with cuts, blisters, scrapes, burns, insect bites to soothe the skin. The Skin therapeutic composition 1 may reduce inflammation, histamine reactions, and/or promote healing when applied to the skin.

The Skin therapeutic composition 2 may be utilized post medical and/or cosmetic procedures, such as ablation and/or non-ablation laser procedures, chemical peels, injections, surgeries, etc. The Skin therapeutic composition 2 may reduce inflammation, redness, dryness, and/or healing times. The Skin therapeutic composition 2 may improve outcomes (e.g., by inhibiting prolonged inflammation which may cause hyper-pigmentation and/or scarring). The Skin therapeutic composition 2 may soothe skin when applied.

minutes. The Skin Therapeutic Compound 2 balm may be applied approximately 2-3 times daily until significant improvement in the area of skin in which the balm is applied (e.g., skin returns to normal, healthy, and/or otherwise expected condition). In some implementations, the Skin Therapeutic Compound 2 balm may be applied more or less frequently than daily. For example, the Skin Therapeutic Compound 2 balm may be applied as directed by a user (e.g., to calm skin, when tightness due to dryness and/or inflammation is felt by user, etc.).

In some implementations, the Skin Therapeutic Compound 2 balm may be utilized post treatment and over open or ablated skin. In some implementations, use of a silicone based Skin Therapeutic Compound 2 balm may increase user satisfaction with the product application in the approximately 24 hours after treatment since the balm may not cause a burning sensation but rather soothe the skin. Application of the Skin Therapeutic Compound 2 in the approximately 24 hours after treatment may decrease hyper-pigmentation, and/or aging. Prolonged post-procedure inflammation has been associated with changes in the skin that may cause scarring, hyper-pigmentation, and/or increased aging in the treated area. Thus, the anti-inflammatory and/or healing promotion provided by the Skin Therapeutic Compound 2 balm may reduce scarring, hyper-pigmentation and/or increased aging associate with prolonged post-procedure inflammation.

The Skin Therapeutic Compound 2 balm may be applied to minor cuts, irritations, skin inflammations, itchiness, folliculitis, insect bites, and/or red skin to promote skin health (e.g., by reducing inflammation, protecting skin, soothing skin, reducing redness, inhibiting harmful microbe growth, etc.) In some implementations, the Skin Therapeutic Compound 2 balm, when applied to an area, may provide a seal (e.g., inhibit and/or block) air and environmental irritants.

In some implementations, the Skin Therapeutic Compound 2 balm may reduce dehydration and/or itching. Since dehydrated skin may not and/or may be slower to repair itself, inhibiting dehydration by application of the Skin Therapeutic Compound 2 balm may promote self-repair of the skin.

In some implementations, the Skin Therapeutic Compound 2 balm may not include emulsifiers to reduced chances of irritation and to provide a balm that is appropriate for use on damaged skin (e.g., post-treatment skin, such as skin that has been laser resurfaced, chemically peeled, micro-needled, to which microderm abrasion has been performed, involved in surgeries, and/or combinations thereof).

Example 5

A skin therapeutic, Skin Therapeutic Composition 3, was prepared by mixing approximately 6 percent to approximately 8 percent *Brassica olearacea italica* Seed Oil, approximately 0.1 percent to approximately 0.3 percent *Zingiber Officinales*, and at least 0.02 percent bisabolol. The Skin Therapeutic Composition 3 may include more bisabolol than *Zingiber Officinales* in some implementations. For example, the Skin Therapeutic 3 may include up to approximately 1 percent more bisabolol than *Zingiber Officinales*. The third skin therapeutic may include approximately 5 percent of *Simmondsia chinensis* Seed oil (Jojoba) and/or lanolin. The third skin therapeutic may include approximately 3 percent by weight of a combination of hexyldecanol, additional bisabolol, cetylhydroxyproline palmitide, stearic acid, and/or *Brassica campestirs* (Rapeseed) Sterols. The Skin Therapeutic Composition 3 may include approximately 4 percent of sunflower seed oil, in some implementations.

Example 6

A lip balm may be prepared including the Skin Therapeutic Composition 3. The Skin Therapeutic Compound 3 may be utilized as for lip relief. For example, the Skin Therapeutic Compound 3 may improve the health of the skin of a lip when applied to a user's lip. The lip balm may include approximately 0.3 percent fragrance, in some implementations.

The Skin Therapeutic Compound 3 may be applied (e.g., topically administered) to skin on and/or proximate a user's lip. The Skin Therapeutic Compound 3 may be applied on any appropriate schedule and/or as often as a user would like, in some implementations. For example, Skin Therapeutic Compound 3 may be applied daily (e.g., morning and/or night) and/or when lips feel dry. The Skin Therapeutic Compound 3 may restore lost moisture, add color (e.g., allow natural coloring of a user to be more present due to increased blood flow), accelerate healing (e.g., due to dry lips, chapped lips, cracked lips, lips on which treatment has been applied such as lip injections and/or Botox, etc.), reduce inflammation (e.g., due to dry and/or cracked lips), reduce moisture loss (e.g., when compared with not using the Skin Therapeutic Compound 3), reduce the appearance of fine lines and/or wrinkles (e.g., by promoting collagen and/or elastin production). The Skin Therapeutic Compound 3 may provide natural UVB protection, in some implementations. User satisfaction with lip health and/or the Skin Therapeutic Compound 3 may be increased with application of the Skin Therapeutic Compound 3 by leaving lips feeling smooth, soft and/or hydrated after application.

In some implementations, the Skin Therapeutic Compound 3 may include fragrance such as spearmint and/or eucalyptus. The fragrance may have therapeutic effects. For example, spearmint and/or eucalyptus may calm and/or reduce stress, which may help post operative healing.

Example 7

A skin therapeutic, Skin Therapeutic Composition 4, was prepared by mixing approximately 5 percent to approximately 10 percent *Brassica olearacea italica* Seed Oil, approximately 0.1 percent bisabolol and approximately 0.1 percent *Zingiber Officinales*, approximately 0.1 to approximately 0.5 percent silver, and approximately 4 to approximately 6 percent by weight of sunflower oil. The Skin Therapeutic Composition 4 may include approximately 3 percent to approximately 5 percent by weight of a combination of hexyldecanol, additional bisabolol, cetylhydroxyproline palmitide, stearic acid, and/or *Brassica campestirs* (Rapeseed) Sterols. In some implementations, the Skin Therapeutic composition 4 may include more bisabolol than *Zingiber Officinales* (e.g., up to approximately 80 percent more bisabolol). The Skin Therapeutic Composition 4 may include approximately 1 to approximately 5 percent by weight of soothing compound(s), such as a mixture of trideceth-9, PEG-5 isononanoate and/or water.

The Skin Therapeutic Composition 4 may be applied (e.g., topically) to the skin on a periodic basis and/or as desired by the user.

Example 8

A soothing cream may be prepared that includes the Skin Therapeutic Composition 4.

Application of the Skin Therapeutic Compound 4 cream may improve dehydrated, dry, cracked, red, sensitive, and/or inflamed skin. In some implementations, the Skin Therapeutic Compound 4 may improve dry skin in approximately 24 hours or less. In some implementations, application of the Skin Therapeutic Compound 4 cream may increase healing (e.g., when compared with skin treated with commercially available moisturizers) by repairing the protective barrier. In some implementations, the Skin Therapeutic Compound 4 cream may protect and/or promote healing in skin with eczema and/or rosacea. In some implementations, Skin Therapeutic Compound 4 cream may inhibit growth of bacteria (e.g., antibacterial properties) and/or inhibit odor-forming bacteria. Application of the Skin Therapeutic Compound 4 cream on skin may have occlusive properties.

The Skin Therapeutic Compound 4 may be used in combination with the Skin Therapeutic Compound 2 balm, in some implementations. For example, Skin Therapeutic Compound 2 balm may be applied for approximately 24 hours after a treatment (e.g., microdermabrasion, medical operations, chemical peels, etc.) and/or after burns. The Skin Therapeutic Compound 2 balm may be applied to broken and/or open skin. Approximately 24 hours after the treatment, the Skin Therapeutic Compound 4 cream may be applied to the skin. In some implementations, the Skin Therapeutic Compound 4 may be utilized to increase hydration of the skin. In some implementations, application of the Skin Therapeutic Compound 4 cream may reduce itching.

In some implementations, the Skin Therapeutic Compound 4 cream may be used in combination with the Skin Therapeutic Compound 1 cleanser. For example, a user may cleanse skin with Skin Therapeutic Compound 1 cleanser. The user may then apply the Skin Therapeutic Compound 4 cream to the skin and/or dehydrated areas of the skin. The Skin Therapeutic Compound 4 cream may be applied daily, periodically, and/or as desired by a user. For example, the Skin Therapeutic Compound 4 cream may be applied by the user when experiencing itchy, scaly, peeling, and/or itchy skin to improve these conditions.

A Skin Therapeutic Composition 4 cream may be topically applied to a user's skin. In some implementations, the Skin Therapeutic Compound 4 cream may be applied to a user's skin approximately 24 hours after an ablative treatment. For example, pain and/or discomfort may occur if applied on open and/or ablated skin prior to approximately 24 hours (e.g., after which skin may have at least partially healed). In some implementations, the Skin Therapeutic Compound 4 cream may reduce dehydration and/or itching.

Example 9

A Skin Therapeutic Composition 5 was prepared by mixing approximately 5 percent to approximately 10 percent *Brassica olearacea italica* Seed Oil, approximately 0.2 percent to approximately 1 percent bisabolol, and approximately 1 percent *Zingiber Officinales*, 5 percent sunflower seed oil, approximately 1 percent sulforaphane, and approximately 2 percent retinyl palmitate. In some implementations, the Skin Therapeutic may include more bisabolol than *Zingiber Officinales*. The Skin Therapeutic Composition 5 may include approximately 2 percent of a combination of hexyldecanol, additional bisabolol, cetylhydroxyproline palmitide, stearic acid, and/or *Brassica campestirs* (Rapeseed) Sterols. The Skin Therapeutic Composition 5 may include approximately 10 percent by weight of sunflower wax and/or another wax, such as a mixture of glyceryl debehenate, tribehenin, and/or glyceryl behenate.

The Skin Therapeutic Composition 5 may be applied (e.g., topically) to the skin on a periodic basis and/or as desired by the user.

Example 10

Figure 2:
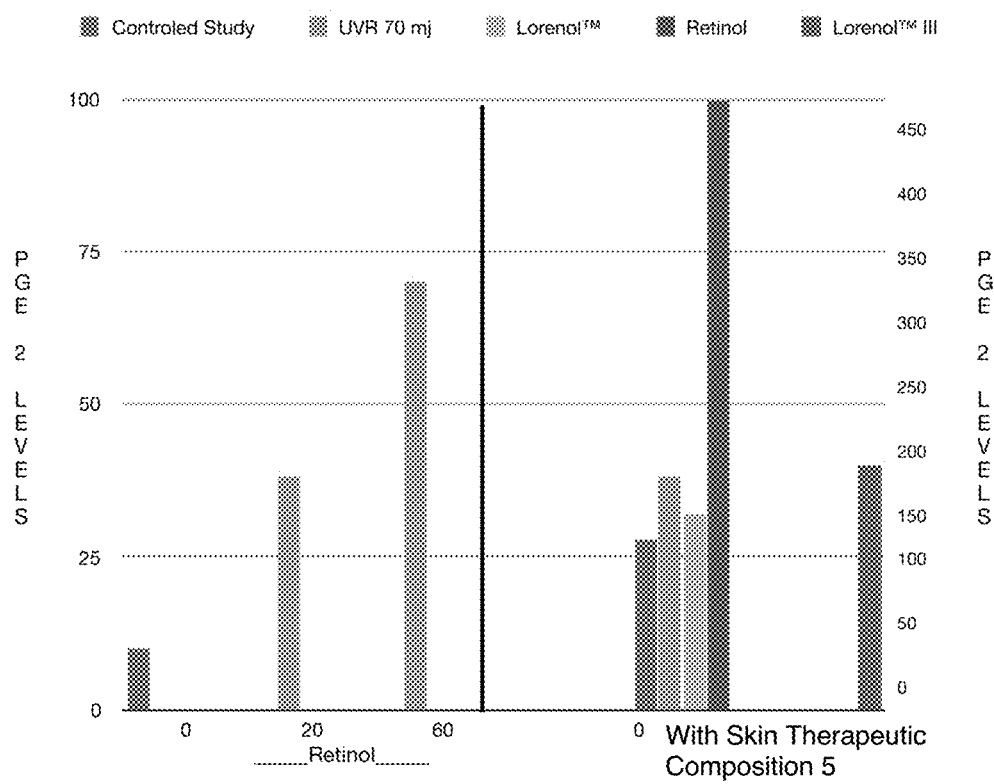
FIG. 2 illustrates an implementation of the reduction and/or inhibition of skin inflammation as a result of topical application of Skin Therapeutic Composition 5.

A night serum may be prepare including Skin Therapeutic Composition 5. FIG. 2 illustrates an implementation of the reduction and/or inhibition of skin inflammation as a result of topical application of Skin Therapeutic Composition 5. FIG. 2 illustrates an increase in PGE-2 in a control study, when Retinol is applied, and when Skin Therapeutic Composition 5 is applied. As illustrated, PGE-2 shows an increase in PGE-2 in the presence of UVR when using Retinol, which explains why it is easier to get a sunburn while using ordinary Retinol products. Skin Therapeutic Composition 5 has the ability to inhibit the increase in PGE-2 caused by UVR exposure. Skin Therapeutic 5 encourages collagen growth and inhibits the overproduction of PGE-2 when exposed to UVR.

Example 11

A Skin Therapeutic Composition 6 was prepared by mixing approximately 5 percent to approximately 10 percent by weight of *Brassica olearacea italica* Seed Oil, approximately 0.15 percent by weight of bisabolol, and approximately 0.15 percent by weight of *Zingiber Officinales*, and approximately 7 percent by weight of Tetrahexyl Ascorbate and/or vitamin C. In some implementations, the Skin Therapeutic Composition 6 may include more bisabolol than *Zingiber Officinales* (e.g., up to approximately 60 percent more bisabolol). The skin therapeutic composition may include approximately 4 percent by weight of a combination of hexyldecanol, additional bisabolol, cetylhydroxyproline palmitide, stearic acid, and/or *Brassica campestirs* (Rapeseed) Sterols. The Skin Therapeutic Composition 6 may include approximately 10 percent by weight of a mixture of glyceryl debehenate, tribehenin, and/or glyceryl behenate.

The Skin Therapeutic Composition 6 may be applied (e.g., topically) to the skin on a periodic basis and/or as desired by the user.

Example 12

A daily regenerating serum was prepared including the Skin Therapeutic 6. The serum may be utilized daily (e.g., 1 or more times a day), in some implementations. For example, the serum may be utilized as a day serum and applied in the mornings.

Example 13

In some implementations, one or more skin therapeutic compositions may be utilized in combination to treat and/or promote healing in dry and/or cracked skin. For example, Skin therapeutic composition 2 (post treatment balm), Skin therapeutic composition 4 (soothing cream), Skin therapeutic composition 3 (lip balm), and Skin therapeutic composition 1 (cleanser) may be utilized to treat dry skin. A healing kit may be created that includes: Skin therapeutic composition 2 (post treatment balm), Skin therapeutic composition 4 (soothing cream), Skin therapeutic composition 3 (lip balm), and Skin therapeutic composition 1 (cleanser), in some implementations.

For example, skin may be cleansed with Skin therapeutic composition 1 and patted dry. The Skin therapeutic composition 2 may be applied to the dried area of the skin. The Skin therapeutic composition 2 may be allowed to absorb in the skin, and then the Skin therapeutic composition 4 may be applied to the same area or a portion thereof. The process may be repeated daily (e.g., 1× or more a day) and/or as desired by a user (e.g., when skin feels dry).

The Skin therapeutic composition 3 (e.g., lip balm) may be applied to the lips and/or area proximate the lips. For example, since dry lips often accompany dry skin, the Skin therapeutic composition 3 may be applied to the lips.

Application of the Skin therapeutic compositions 1, 2, 3, and/or 4 may provide a protective barrier to guard against water loss (e.g., since water loss may cause inflammatory responses), reduce reaction to irritants such as allergens (e.g., via antihistamine properties of the skin therapeutic compositions(s)), and/or promote repair of the skin. In some implementations, the Skin therapeutic compositions 1, 2, 3, 4 may be capable of providing a protective barrier to the skin with a non-greasy feel.

Example 14

In some implementations, one or more of the skin therapeutic compositions may be utilized post ablative and non-ablative laser procedures. For example, Skin therapeutic composition 2, 4, 1, and 6 may be applied to the skin that underwent the laser procedure. The Skin therapeutic compositions 2, 4, 1, and/or 6 may inhibit long term inflammation, reduce inflammation, decrease pain, decrease itching, and/or soothe the skin. A laser procedure kit may be created that includes skin therapeutic composition 2, 4, 1, and 6.

The Skin therapeutic composition 2 may be applied to the skin after a laser procedure. For example, the Skin therapeutic composition 2 may be applied to the skin 6 or more times daily for the first week. In some implementations, the number of applications may vary based on individual healing. For example, a user may apply fewer or more based on how skin feels to a user (e.g., tight, dry, inflamed, red, hot, etc.). Application of the Skin therapeutic composition 2 may reduce discomfort and promote healing.

The Skin therapeutic composition 4 may be applied as early as 24 hours after the laser procedure. The application of Skin therapeutic composition 4 may reduce flaking.

The Skin therapeutic composition 1 cleanser may be administered daily (e.g., 1× daily, 2× daily, etc.), in some implementations. The Skin therapeutic composition 1 cleanser may be used for 7 or more days, in some implementations.

The Skin therapeutic composition 6 may be applied 72 hours after healing is complete (e.g., red and/or swollen skin is no longer present). The Skin therapeutic composition 6 (e.g., dime size amount) may be applied daily (e.g., evenings).

The Skin therapeutic composition 3 (e.g., lip balm) may be applied as needed by the user (e.g., to relieve dry lips).

In some implementations, the described process may accelerate recovery in as little as 4 days. Commonly used post-operative treatments may only have recovery at 8-16 days. Thus, user satisfaction with the laser procedure and recovery from the laser procedure may be increased by utilizing the described processes.

Example 15

The process described in Example 13 may be performed for chemical peels, surgeries (e.g., breast, facial, liposuction), and/or in-office procedures (e.g., injectables). The application of Skin therapeutic composition(s) may decrease inflammation and/or promote healing (e.g., to reduce recovery time). A kit that includes one or more of the compositions may be created.

Example 16

The skin therapeutic compositions may be utilized before and/or after micro-needling procedures, in some implementations. For example, Skin therapeutic composition 1, 2, 3, and 4 may be utilized. A kit may be created that includes Skin therapeutic composition 1, 2, 3, and 4. The application of the Skin therapeutic composition(s) may decrease signs of aging, increase collagen and/or elastin production, and/or accelerate skin recovery after treatment. In some implementations, the Skin therapeutic composition(s) may soothe the skin, post-treatment, by inhibiting air from contacting the treated area (e.g., by providing a protective barrier), reduce pain, reduce redness, and/or increase comfort. A microneedling procedure kit may be created that includes skin therapeutic composition 1, 2, 3, and/or 4.

The Skin therapeutic composition 2 may be applied before and/or after the micro-needling procedure. The Skin therapeutic composition 2 may reduce redness, pain, and/or inflammation due to the procedure. The application of Skin therapeutic composition 2 may accelerate healing and/or improve outcomes (e.g., by reducing scarring and/or hyperpigmentation due to prolonged inflammation). The Skin therapeutic composition 2 may be applied daily.

The Skin therapeutic composition 4 may be applied approximately 24 hours after treatment. The Skin therapeutic composition 4 may decrease dehydration and/or itching.

In some implementations, prior to micro-needling procedures, the Skin therapeutic composition 1 cleanser may be applied daily (e.g., 1× day, 2× day, etc.) and Skin therapeutic composition 6 may be applied to the dried area. For example, this pre-procedure may be performed days and/or weeks before the procedure. After the micro-needling procedure, the Skin therapeutic composition 2 may be applied (e.g., liberally) to treated areas. In some implementations, the Skin therapeutic composition 2 may be applied several times daily and/or based on user preference.

In some implementations, beginning the morning after the micro-needling procedure, the skin may be washed with the Skin therapeutic composition 4 cleanser (e.g., 1× daily and/or 2× daily). The Skin therapeutic composition 2 may be applied to dried skin (e.g., patted dry after the cleanser). The Skin therapeutic composition 4 may be applied several times a day, 24 hours after the micro-needling procedure. After 72 hours and/or after healing is complete (e.g., no visibly red and/or swollen regions), the Skin therapeutic composition 6 may be applied daily (e.g., evenings). In some implementations, the Skin therapeutic composition 6 may be applied for at least next 4 days.

Example 17

In some implementations, a combination of skin therapeutic compositions may be applied post medically ablated skin treatments. For example, Skin therapeutic composition 1, 2, 3, 4, and/or 6 may be utilized. The combination of skin therapeutic compositions may reduce inflammation, redness, pain, scarring, and/or down time after the procedure. In some implementations, the non-greasy feel of the skin therapeutic compositions may encourage use and/or inhibit excessive dehydration of the skin. A post medically ablated skin kit may be created that includes skin therapeutic composition 1, 2, 3, 4 and/or 6.

The Skin therapeutic composition 2 may be applied (e.g., in the place of Aquaphor®) up to 6 times daily after the skin procedure. The Skin therapeutic composition 2 may be applied for a week, in some implementations. The Skin therapeutic composition 1 cleanser may be utilized to cleanse skin daily (e.g., 1-2 times daily). The Skin therapeutic composition 4 cleanser may be utilized for at least a week, in some implementations. After healing is complete (e.g., pink but not red skin) and/or sutures removed, Skin therapeutic composition 6 may be utilized daily (e.g., evenings). In some implementations, the Skin therapeutic composition 6 may be applied for 3 or more days. In some implementations, Skin therapeutic composition 4 may be utilized for increasing skin hydration and/or to reducing skin flaking. The Skin therapeutic composition 4 may be utilized daily (e.g., 1× day, 2× day) 24 hours after the skin procedure.

Example 18

The skin therapeutic composition(s) may be utilized after tattoo removal procedures. For example, Skin therapeutic composition 2, 1, and 6 may be utilized in combination. The application of the combination of the Skin therapeutic compositions may reduce inflammation and/or pain. The application of Skin therapeutic compositions may facilitate minimizing scarring, which may increase user satisfaction with the procedure. A tattoo removal kit may be created that includes skin therapeutic composition 1, 2, and/or 6.

The Skin therapeutic composition 2 may be applied daily (e.g., up to 6 times daily) after the tattoo removal procedure. The Skin therapeutic composition 1 may be used in place of Aquaphor® to improve outcomes (e.g., improve recovery times and/or decrease down time). The Skin therapeutic composition 1 cleanser may be utilized to cleanse skin daily (e.g., 1-2× day). The Skin therapeutic composition 1 may be utilized to cleanse skin for at least a week, in some implementations. 72 hours after treatment, the Skin therapeutic composition 2 and the Skin therapeutic composition 6 may be applied daily. For example, the Skin therapeutic composition 2 may be applied in the morning (e.g., after drying the skin after cleansing) and the Skin therapeutic composition 6 may be applied in the evening (e.g., after drying the skin after cleansing). In some implementations, when a user is known to keloid (e.g., based on previous procedures), Skin therapeutic composition 6 may be applied in the morning and evening.

End of Examples

In the described Examples, specific proportions of ingredients, specific manufacturing processes, specific kits, and specific administration techniques have been described. These Examples are provided as non-limiting examples of implementations of the skin therapeutic, methods of manufacture, and administration schedules, other implementations may be utilized as appropriate. In addition, one or more of the implementations or portions thereof described in one or more of the Examples may be utilized in combination with other implementations described in one or more Examples.

In various implementations, one or more skin therapeutic compositions may include formulations or portions of formulations, as described herein. Skin therapeutic compositions may be produced or at least partially produced, as described herein.

In various implementations, a skin therapeutic may include at least two of: *Brassica olearacea italica* Seed Oil, bisabolol, and/or *Zingiber Officinales*. The *Brassica olearacea italica* Seed Oil may comprises up to approximately 10 percent by weight of the skin therapeutic. The bisabolol may comprise up to approximately 10 percent by weight of the skin therapeutic. The *Zingiber Officinales* may comprise up to approximately 10 percent by weight of the skin therapeutic.

In various implementations, a topical skin composition may include approximately 0.025 to approximately 0.1 weight percent of *Zingiber Officinale*; at least approximately 0.25 weight percent of Bisabolol; and approximately 6 to approximately 8 weight percent of *Brassica olearacea italica* Seed oil. The topical skin composition may include approximately 10 to approximately 20 weight percent sunflower oil (e.g., approximately 15% by weight of sunflower oil). The topical skin composition may be a balm and may not include added water (e.g., to reduce irritation of sensitive skin). The topical administration of the skin composition may improve skin health, for example, by reducing redness, inflammation, healing time, recovery time, visible effects of aging, etc.

In various implementations, a topical skin composition may include approximately 0.05 to approximately 0.15 weight percent of *Zingiber Officinale*; approximately 0.05 weight percent to approximately 0.15 weight percent of Bisabolol; and/or approximately 5 to approximately 10 weight percent of *Brassica olearacea italica* Seed oil. The topical skin composition may include silver and/or sunflower oil. For example, the topical skin composition may include less than 20 percent silver (e.g., approximately 0.1 to approximately 10% silver, approximately 0.1 to approximately 0.5% silver). The topical skin composition may include less than 10 percent sunflower oil (e.g., approximately 0.1 to approximately 10% sunflower oil, approximately 4 to approximately 6% sunflower oil). Topical application of the skin composition may soothe skin. The topical administration of the skin composition may improve skin health, for example, by reducing redness, inflammation, healing time, recovery time, visible effects of aging, etc.

In various implementations, a topical skin composition may include approximately 0.01 to approximately 1.5 weight percent of *Zingiber Officinale*; approximately 0.01 to approximately 1.5 weight percent of Bisabolol; and approximately 5 to approximately 10 weight percent of *Brassica olearacea italica* Seed oil. The skin composition may be a cream, lotion, and/or serum applied periodically (e.g., daily) and/or as desired. The topical skin composition may include sunflower wax and/or sulforaphane. The topical skin composition comprising sulforaphane may be applied at night (e.g., periodically and/or as desired). The topical skin composition may include less than approximately 10 weight percent sulforaphane (e.g., approximately 1% to approximately 4% by weight of sulforaphane, approximately 0.5 to approximately 1.5% by weight sulforaphane). The topical skin composition may include vitamin C and/or Tetrahexyl Ascorbate. The topical administration of the skin composition may improve skin health, for example, by reducing redness, inflammation, healing time, recovery time, visible effects of aging, etc.

In various implementations, one or more or more of the skin therapeutics singularly and or in combination with other skin therapeutics or other skin care products may be administered, as described herein. The skin therapeutic composition(s) may be administered according to one or more of the described treatment regiments. Topical administration of the skin therapeutic may improve skin health (e.g., reduce redness, reduce visible signs of aging, reduce inflammation, reduce recovery time, promote healing, etc.). The skin therapeutic composition may be topically administered to healthy skin, before skin receives a skin procedure, after skin receives a skin procedure, and/or to otherwise damaged skin (e.g., burned, dry, cracking, etc.).

In various implementations, one or more substitute compositions may be utilized in place, in partial replacement of, and/or in conjunction with one or more of the described components of the skin therapeutics. The substitute compositions may or may not substantially impact the efficacy of the skin therapeutics (e.g., based on the quantity of the substitute utilized and/or the user). The substitute compositions may be utilized for any appropriate reason, such as cost reduction, user sensitivity (e.g., allergy), treatment characteristics, user preferences (e.g., organic ingredients, non-GMO ingredients, etc.). For example, coconut oil may be utilized in one or more of the described skin therapeutics in place of at least a portion of the *Brassica olearacea italica* Seed Oil. The coconut oil may be utilized in addition to the quantity of the *Brassica olearacea italica* Seed Oil utilized in a skin therapeutic in some implementations. For example, a user with *Brassica olearacea italica* Seed Oil sensitivity may utilize a skin therapeutic with at least a portion of the *Brassica olearacea italica* Seed Oil replaced by coconut oil.

As another example, clove oil may be used in one or more of the described skin therapeutics in place of at least a portion of the bisabolol and/or the *Zingiber Officinales*. The clove oil may be utilized in addition to the quantity of the bisabolol and/or *Zingiber Officinales* in a skin therapeutic in some implementations.

As another example, sunflower oil and/or sunflower wax may be utilized in one or more of the described skin therapeutics in place of at least a portion of a mixture of glyceryl debehenate, tribehenin, glyceryl benhenate, and/or other high melting point lipids. The sunflower oil and/or sunflower wax may be used in addition to the quantity of the mixture of a mixture of glyceryl debehenate, tribehenin, and/or glyceryl behenate in a skin therapeutic, in some implementations.

As another example, ethyl vanillin may be utilized in one or more of the described skin therapeutics in place of at least a portion of sunflower seed oil. The ethyl vanillin may be utilized in addition to the quantity of the sunflower seed oil in a skin therapeutic in some implementations.

In various implementations, components of compositions (e.g., skin therapeutics) are identified as percentage by weight based on the total weight of the composition, unless indicated to the contrary.

In various implementations, the skin therapeutics and/or portions thereof may be natural and/or organic. For example, natural (e.g., purified from a natural source and/or produced by microorganisms) and/or synthetic *Zingiber Officinales* may be utilized.

Although several compounds have been described specifically, other forms such as derivatives of the described compounds may be utilized, as appropriate in place of and/or in combination with the described compounds. In various implementations, purified and/or non-purified compositions including the described compounds may be utilized. In some implementations, described compounds may be utilized in liquid (e.g., oil, cream, etc.) and/or solid (e.g., wax, powder) form.

Administration methods may be implemented by various implementations of the skin therapeutics. In addition, various operations of the administration methods may be added, deleted, and/or modified.

Kits may be created that include one or more skin therapeutic compositions. The kits may be for use in treating a condition, maintaining skin health, and/or improving skin health. One or more kits may be used in conjunction with one or more other kits and/or individual skin treatment compositions. A kit may include one or more of any of the described skin therapeutic compositions. The kit may include one or more smaller quantities (e.g., less than the other products and/or less than an administration quantity of the product) of one or more skin therapeutic compositions to allow users to sample other skin therapeutic compositions (e.g., a small sample of the lip balm may be included in the daily regimen). In some implementations, the kit may include other treatments, such as Aquaphor®, other cleansers, other creams, prescription topical treatments, etc. The kit may include instructions that include administration regimens and/or information related to products in the kit. The kit may include administration aids (e.g. dispensing tools such as spoons, pads, and/or pumps; wipes for cleansing skin and/or tools; etc.).

Although users have been described as a human, a user may be a person, a group of people, and/or one or more people applying the described skin therapeutic on one or more other people.

It is to be understood the implementations are not limited to particular systems or processes described which may, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. Thus, for example, reference to "a wax" includes a combination of two or more waxes and reference to "skin therapeutic" includes different types and/or combinations of skin therapeutics.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A topical skin composition cream comprising:
    approximately 0.025 to approximately 1 weight percent of Zingiber Officinale;
    at least approximately 0.15 weight percent of Bisabolol;
    approximately 0.05 to approximately 10 weight percent of Brassica olearacea italica Seed oil; and
    a binder, wherein the binder allows the topical skin composition to be a cream delivery form;
    wherein topical administration of the skin cream reduces inflammation and redness of skin.

2. The topical skin cream of claim 1 wherein an amount by weight percent of Bisabolol in the topical skin cream is greater than an amount by weight percent of Brassica olearacea italica Seed oil in the skin cream.

3. A topical skin cleanser comprising:
    approximately 0.025 to approximately 1 weight percent of Zingiber Officinale;
    approximately 0.025 to approximately 0.15 weight percent of Bisabolol;
    approximately 0.05 to approximately 10 weight percent of Brassica olearacea italica Seed oil; and
    approximately 5-10 weight percent of Sodium C-14-16 olefin sulfonate, wherein the Sodium C-14-16 olefin sulfonate allows the topical skin composition to be a cleanser delivery form;
    and wherein topical administration of the skin cleanser reduces inflammation and redness of skin;
    and wherein topical administration of the skin cleanser cleanses the skin.

4. The topical skin cream of claim 1 wherein the weight percentage of Zingiber Officinale is approximately 0.025 to approximately 0.1 weight percent of the skin cream, and wherein the weight percentage of Bisabolol is at least approximately 0.025, and wherein the weight percentage of Brassica olearacea italica Seed oil is approximately 6 to approximately 8 weight percent of the skin cream, and wherein the skin cream further comprises approximately 10-20 weight percent of sunflower oil.

5. The topical skin cream of claim 1 wherein the weight percentage of Zingiber Officinale is approximately 0.1 to approximately 0.3 weight percent of the skin cream, and wherein the weight percentage of Brassica olearacea italica Seed oil is approximately 6 to approximately 8 weight percent of the skin composition, and wherein the skin cream further comprises approximately 4-6 weight percent of at least one of:
    jojoba,
    lanolin,
    or mixtures thereof;
    and wherein the skin cream is a lip balm.

6. The topical skin cream of claim 1 wherein the weight percentage of Zingiber Officinale is approximately 0.5 to approximately 1.5 weight percent of the skin cream, and wherein the weight percentage of Bisabolol is approximately 0.5 to approximately 1.5 weight percent of the skin cream, and wherein the skin cream further comprises approximately 0.1 to approximately 0.4 of silver, and wherein the skin cream further comprises approximately 10 to approximately 20 weight percent of sunflower oil, and wherein topical administration of the skin cream soothes the skin.

7. The topical skin cream of claim 1 wherein the weight percentage of Zingiber Officinale is approximately 0.8 to approximately 1 weight percent of the skin cream, and wherein the weight percentage of Brassica olearacea italica Seed oil is approximately 5 to approximately 10 weight percent of the skin composition, and wherein the skin cream further comprises:
    approximately 0.5 to approximately 1.5 weight percent of sulforaphane;
    approximately 4 to approximately 6 weight percent of sunflower oil;
    approximately 1 to approximately 3 weight percent of retinyl palmitate;
    Brassica campestirs (Rapeseed) Sterols;
    approximately 4 to approximately 6 weight percent of at least one of sunflower wax or another wax.

8. The topical skin cream of claim 1 wherein the weight percentage of Zingiber Officinale is approximately 0.1 to approximately 0.2 weight percent of the skin cream, and wherein the weight percentage of Bisabolol is approximately 0.15 to approximately 0.2 weight percent of the skin cream, and wherein the weight percentage of Brassica olearacea italica Seed oil is approximately 5 to approximately 10 weight percent of the skin cream, and wherein the skin cream further comprises approximately 6 to approximately 8 of at least one of Tetrahexyl Ascorbate, Vitamin C, or mixtures thereof.

9. The topical skin cream of claim 1 wherein improving skin health comprises at least one of: reducing redness, reducing inflammation, reducing skin recovery time, or reducing dryness.

10. The topical skin cream of claim 1 wherein the skin cream is applied to healthy skin.

11. A method of administration to reduce inflammation and redness of skin, the method comprising topically administering on at least a portion of the skin a therapeutically effective amount of a skin cream, the skin cream comprising:
    approximately 0.025 to approximately 1 weight percent of Zingiber Officinale;
    at least approximately 0.15 weight percent of Bisabolol; and
    approximately 0.05 to approximately 10 weight percent of Brassica olearacea italica Seed oil; and a binder, wherein the binder allows the topical skin composition to be a cream delivery form.

12. The method of claim 11 wherein the skin cream is topically administered to at least one of burned skin or dry skin.

13. The method of claim 11 wherein the skin cream is topically administered after one or more skin treatments, and wherein at least one of the skin treatments comprises surgery, chemical peel, mircroneedling, microderm abrasion, injections, ablative laser therapy, or non-ablative laser therapy.

14. The method of claim 11 wherein the skin cream is topically administered prior to one or more skin treatments.

15. The method of claim 11 wherein administration of the therapeutically effective amount of the topical skin cream at least one of increases the rate of skin healing or decreases scarring.

16. The method of claim 11 wherein the skin cream is topically administered after one or more skin treatments, and wherein at least one of the skin treatments comprises surgery, chemical peel, or tattoo removal treatment.

17. The skin cream of claim 1 further comprising approximately 0.5 to approximately 1.5 weight percent of sulforaphane.

18. A topical skin cream of claim 1
wherein the skin cream comprises a molecular weight of less than 500 Daltons.

19. The skin cleanser of claim 3 further comprising approximately 0.5 to approximately 1.5 weight percent of sulforaphane.

20. The method of claim 11 wherein the skin cream further comprises approximately 0.5 to approximately 1.5 weight percent of sulforaphane.

* * * * *